United States Patent
Pulst

(10) Patent No.: US 6,673,535 B1
(45) Date of Patent: Jan. 6, 2004

(54) METHODS OF DETECTING SPINOCEREBELLAR ATAXIA-2 NUCLEIC ACIDS

(75) Inventor: Stefan M. Pulst, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/083,268

(22) Filed: May 22, 1998

Related U.S. Application Data

(62) Division of application No. 08/727,084, filed on Oct. 8, 1996, now abandoned.
(60) Provisional application No. 60/022,207, filed on Jul. 19, 1996, and provisional application No. 60/017,388, filed on May 8, 1996.

(51) Int. Cl.$^7$ ............................ C12Q 1/68; C07H 21/04

(52) U.S. Cl. ..................... 435/6; 435/91.2; 435/320.1; 536/23.1; 536/24.3; 536/24.33

(58) Field of Search ............................. 536/23.1, 24.33, 536/24.31; 435/6, 320.1, 325, 91.2

(56) References Cited

U.S. PATENT DOCUMENTS

| | | | |
|---|---|---|---|
| 5,155,218 A | 10/1992 | Weinshank et al. | ............ 536/27 |
| 5,474,796 A | 12/1995 | Brennan | .................... 427/2.13 |
| 5,552,282 A | 9/1996 | Caskey et al. | |
| 5,650,270 A | 7/1997 | Giese et al. | |
| 5,650,277 A | 7/1997 | Navot et al. | |
| 5,741,645 A | 4/1998 | Orr et al. | |
| 5,853,995 A * | 12/1998 | Lee | ................................. 435/6 |
| 5,885,834 A | 3/1999 | Epstein | ........................ 435/375 |
| 6,251,589 B1 | 6/2001 | Tsuji et al. | |

FOREIGN PATENT DOCUMENTS

| | | |
|---|---|---|
| WO | WO 95/01437 | 1/1995 |
| WO | WO 97/17445 | 5/1997 |
| WO | 97/18224 | 5/1997 |

OTHER PUBLICATIONS

Sanpei, et al., "Direct Detection of Expanded (CAG/CTG) Repeats in the Myotonin–protein Kinase Genes of Myotonic Dystrophy Patients Using a High–Stringency Hybridization Method", *Biochemical and Biophysical Research Communications*, 212(2), 341–346 (Jul. 17, 1995).

National Center for Biotechnology Information, National Library of Medicine, National Institutes of Health, Blast 2 Sequence results of gi 4506794 and gi 12382830 [online]. Bethesda, MD [retrieved on Nov. 26, 2001]. Retrieved from the Internet:<URL:http://www.ncbi.nlm.nih.gov/blast/bl2seq/wblast2.cgi>, 2 pages.

National Center for Biotechnology Information. National Library of Medicine, National Institutes of Health, Blast 2 Sequence results of gi 4506794 and gi 12382831 [online]. Bethesda, MD [retrieved on Nov. 26, 2001]. Retrieved from the Internet:<URL:http://www.ncbi.nlm.nih.gov/blast/bl2seq/wblast2.cgi>, 2 pages.

National Center for Biotechnology Information, National Library of Medicine, National Institutes of Health, Blast 2 Sequence results of gi 4506794 and gi 12382832 [online]. Bethesda, MD [retrieved on Nov. 26, 2001]. Retrieved from the Internet:<URL: http://www.ncbi.nlm.nih.gov/blast/bl2seq/wblast2.cgi>, 2 pages.

National Center for Biotechnology Information, National Library of Medicine, National Institutes of Health, Blast 2 Sequence results of gi 4506794 and gi 12382833 [online]. Bethesda, MD [retrieved on Nov. 26, 2001]. Retrieved from the Internet:<URL: http://www.ncbi.nlm.nih.gov/blast/bl2seq/wblast2.cgi>, 2 pages.

National Center for Biotechnology Information, National Library of Medicine, National Institutes of Health, Blast 2 Sequence results of gi 4506794 and gi 12382834 [onlilne]. Bethesda, MD [retrieved on Nov. 26, 2001]. Retrieved from the Internet:<URL: http://www.ncbi.nlm.nih.gov/blast/bl2seq/wblast2.cgi>, 2 pages.

National Center for Biotechnology Information, National Library of Medicine, National Institutes of Health, Blast 2 Sequence results of gi 4506794 and gi 12382835 [online]. Bethesda, MD [retrieved on Nov. 26, 2001]. Retrieved from the Internet:<URL http://www.ncbi.nlm.nih.gov/blast/bl2seq/wblast2.cgi>, 2 pages.

Choudhry, S., et al., "CAG Repeat Instability at SCA2 Locus: Anchoring CAA. Interruptions and Linked Single Nucleotide Polymorphisms," *Human Molecular Genetics*, 10:2437–3446 (2001).

Mizushima, K., et al., "Analysis of Spinocerebellar Ataxia Type 2 Gene and Haplotype Analysis: $(CGG)_{1-2}$ Polymorphism and Contribution to Founder Effect," *Journal of Medical Genetics*, 36:112–114 (1999).

Sahba, S., et al., "Genomic Structure of the Human Gene for Spinocerebellar Ataxia Type 2 (SCA2) on Chromosome 12q24.1," *Genomics*, 47:359–364 (1998).

(List continued on next page.)

*Primary Examiner*—Jeffrey Fredman
*Assistant Examiner*—Jeanine Goldberg
(74) *Attorney, Agent, or Firm*—Hamilton, Brook, Smith & Reynolds, P.C.

(57) ABSTRACT

The present invention provides isolated nucleic acids encoding human SCA2 protein, or fragments thereof, and isolated SCA2 proteins encoded thereby. Further provided are vectors containing invention nucleic acids, probes that hybridize thereto, host cells transformed therewith, antisense oligonucleotides thereto and compositions containing antibodies that specifically bind to invention polypeptides, as well as transgenic non-human mammals that express the invention protein. In addition, methods for diagnosing spinocerebellar Ataxia Type 2 are provided.

4 Claims, 9 Drawing Sheets

OTHER PUBLICATIONS

IntelliGenetics Sequence Comparison. SEQ ID No.: 2 and 4 and SEQ ID No.: 3 and 5.*

Nagafuchi et al. "Dentatorubral and pallidoluysian atrophy expansion of an unstable CAG trinucleotide on chromosome 12p". Nature Genetics. vol. 6, No. 1, pp. 14–18, 1994.*

Banfi, et al., "Identification and characterization of the gene causing type 1 spinocerebellar ataxia," Nature Genetics, 7, 513–519 (1994).

Belal et al., "Clinical and genetic analysis of a Tunisian family with autosomal dominant cerebellar ataxia type 1 linked to the SCA2 locus," Neurology, 44, 1423–1426 (1994).

Brook, "Retreat of the triplet repeat," Nat. Genet., 3, 279–281 (1993).

Brunner et al., "Brief Report: Reverse Mutation In Myotonic Dystrophy," New Engl. J. Med., 328, 476–480 (1993).

Filla et al., "Prevalence of hereditary ataxias and spastic paraplegias in Molise, a region of Italy," J. Neurol., 239, 351–353 (1992).

Gispert et al., "Chromosomal assignment of the second locus for autosomal dominant cerebellar ataxia (SCA2) to chromosome 12q23–24.1," Nat. Genet., 4, 294–299 (1993).

Imbert, "Cloning of the gene for spinocerebellar ataxia 2 reveals a locus with high sensitivity to expand CAG/glutamine repeats," Nature Genetics, 14, 285–291(1996).

Ioannou et al., "A new bacteriophage P1–derived vector for the propagation of large human DNA fragments," Nat. Genet., 6, 84–89 (1994).

Kawaguchi et al., "CAG expansions in a novel gene for Machado–Joseph disease at chromosome 14q32.1," Nat. Genet., 8, 221–227 (1994).

Koide et al., "Unstable expansion of CAG repeat in hereditary dentatorubral–pallidoluysian atrophy (DRPLA)," Nat. Genet., 6, 9–13 (1994).

Kremer, et al., "Mapping of DNA Instability at the Fragile X to a Trinucleotide Repeat Sequence p(CCG)n," Science, 252, 1711–1714 (1991).

Lopes–Cendes et al., "Confirmation of the SCA–2 Locus as an Alternative Locus for Dominantly Inherited Spinocerebellar Ataxias and Refinement of the Candidate Region," Am. J. Hum. Genet., 54, 774–781 (1994).

MacDonald et al., "A Novel Gene Containing a Trinucleotide Repeat That Is Expanded and Unstable on Huntington's Disease Chromosomes," Cell, 72, 971–983 (1993).

Mahadevan, et al., "Myotonic Dystrohpy Mutation: An Unstable CTG Repeat in the 3' Untranslated Region of the Gene," Science, 255, 1253–1255 (1992).

Mandel, "Questions of expansion," Nat. Genet., 4, 8–9 (1993).

Nagafuchi et al., "Dentatorubral and pallidoluysian atrophy expansion of an unstable CAG trinucleotide on chromosome 12p,"Nat. Genet., 6, 14–18 (1994).

Orr et al., "Expansion of an unstable trinucleotide CAG repeat in spinocerebellar ataxia type 1," Nat. Genet., 4, 221–226 (1993).

Polo et al., "Heredetiary Ataxias and Paraplegias in Cantabria, Spain," Brain, 114, 855–866 (1991).

Pulst et al., "Anticipation in spinocerebellar ataxia type 2," Nat. Genet., 5, 8–10 (1993).

Pulst et al., "Genetic and Physical Map of the Spinocerebellar Ataxia 2 (SCA2) Region on Human Chromosome 12," Neurology, 45, A422 (1995).

Pulst et al., "Moderate expansion of a normally biallelic trinucleotide repeat in spinocerebellar ataxia type 2," Nature Genetics, 14, 269–276 (1996).

Ranum et al., "Spinocerebellar ataxia type 5 in a family descended from the grandparents of President Lincoln maps to chromosome 11," Nat. Genet., 8, 280–284 (1994).

Rubensztein, et al., Phenotypic Characterization of Individuals with 30–40 CAG Repeats in the Huntington Disease (HD) Gene Reveals HD Cases with 36 Repeats and Apparently Normal Elderly Individuals with 36–39 Repeats, Am. J. Hum. Genet., 59, 16–22 (1996).

Sanpei et al., "Identification of the spinocerebellar ataxia type 2 gene using a direct identification of repeat expansion and cloning technique, DIRECT," Nature Genetics, 14, 277–284 (1996).

Stevanin et al., "Screening for proteins with polyglutamine expansions in autosomal dominant cerebellar ataxias," Human Molecular Genetics, 5, 1887–1892 (1996).

Takiyama et al., "The gene for Machado–Joseph disease maps to human chromosome 14q," Nat. Genet., 4, 300–304 (1993).

The WashU–Merck ESP Project, "Soares parathyroid tumor NbHPA Homo sapiens cDNA clone," Accession No. W39162, May 15, 1996.

Trottier et al., "Polyglutamine expansions as a pathological epitope in Huntington's disease and four dominant cerebellar ataxias," Letters to Nature, 378, 403–406 (1995).

GenBank Accession No. Y08262, Imbert et al., Sep. 1996.

GenBank Accession No. T78912, Lutz et al., May 1997.

GenBank Accession No. A62706, Tora et al., May 1997.

GenBank Accession No. AA476524, Hillier et al., Jan. 1995.

GenBank Accession No. L27350, Ambrose et al., 1994.

GenBank Accession No. U70323, Pulst et al., Sep. 1996.

GenBank Accession No. AF041472, Nechiporuk et al., Jan. 1998.

"PCT Kits", from 1992/1993 Biotechnology Catalog, Perkin Elmer, pp. 11–12, 1992.

Filla et al., "Has Spinocerebellar Ataxia Type 2 a Distinct Phenotype?", Neurology, 45, 793–796 (Apr. 1995).

* cited by examiner

```
  1  TTGGTAGCAACGGAAACGGCGGCGGCGCGTTTCGGCCCGGCTCCCGGCGGCTCCTTGGTC

61  TCGGCGGGCCTCCCCGCCCCTTCGTCGTCGTCCTTCTCCCCCTCGCCAGCCCGGGCGCCC

121  CTCCGGCCGCGCCAACCCGCGCCTCCCCGCTCGGCGCCCGTGCGTCCCCGCCGCGTTCCG

181  GCGTCTCCTTGGCGCGCCCGGCTCCCGGCTGTCCCCGCCCGGCGTGCGAGCCGGTGTATG
          SCA2-A
241  GGCCCCTCACCATGTCGCTGAAGCCCCAGCAGCAGCAGCAGCAGCAGCAACAGCAGC
                                                       SCA2-B
301  AGCAGCAACAGCAGCAGCAGCAGCAGCAGCAGCCGCCGCCCGCGGCTGCCAATGTCCGCA

361  AGCCCGGCGGCAGCGGCCTTCTAGCGTCGCCCGCCGCCGCGCCTTCGCCGTCCTCGTCCT

421  CGGTCTCCTCGTCCTCGGCCACGGCTCCCTCCTCGGTGGTCGCGGCGACCTCCGGCGGCG

481  GGAGGCCCGGCCTGGGCAG GTGGGTGTCGGCACCCC
```

FIG. 2

```
  1 ACCCCCGAGAAAGCAACCCAGCGCGCCGCCCGCTCCTCACGTGTCCCTCCCGGCCCCGGG    60
 61 GCCACCTCACGTTCTGCTTCCGTCTGACCCCTCCGACTTCCGGTAAAGAGTCCCTATCCG   120
                      *
121 CACCTCCGCTCCCACCCGGCGCCTCGGCGCGCCCGCCCTCCGATGCGCTCAGCGGCCGCA   180
  1                                           M  R  S  A  A  A     6
181 GCTCCTCGGAGTCCCGCGGTGGCCACCGAGTCTCGCCGCTTCGCCGCAGCCAGGTGGCCC   240
  7  A  P  R  S  P  A  V  A  T  E  S  R  R  F  A  A  A  R  W  P    26
241 GGGTGGCGCTCGCTCCAGCGGCCGGCGCGGCGGAGCGGGCGGGGCGGCGGTGGCGCGGCC   300
 27  G  W  R  S  L  Q  R  P  A  R  R  S  G  R  G  G  G  A  A       46
301 CCGGGACCGTATCCCTCCGCCGCCCCTCCCCCGCCGGCCCCGGCCCCCCTCCCTCCCGG    360
 47  P  G  P  Y  P  S  A  A  P  P  P  P  G  P  G  P  P  P  S  R    66
361 CAGAGCTCGCCTCCCTCCGCCTCAGACTGTTTTGGTAGCAACGGCAACGGCGGCGGCGCG   420
 67  Q  S  S  P  P  S  A  S  D  C  F  G  S  N  G  N  G  G  G  A    86
421 TTTCGGCCCGGCTCCCGGCGGCTCCTTGGTCTCGGCGGGCCTCCCCGCCCCTTCGTCGTC   480
 87  F  R  P  G  S  R  R  L  L  G  L  G  G  P  P  R  P  F  V  V   106
481 GTCCTTCTCCCCCTCGCCAGCCCGGGCGCCCCTCCGGCCGCGCCAACCCGCGCCTCCCCG   540
107  V  L  L  P  L  A  S  P  G  A  P  P  A  A  P  T  R  A  S  P   126
541 CTCGGCGCCCGTGCGTCCCCGCCGCGTTCCGGCGTCTCCTTGGCGCGCCCGGCTCCCGGC   600
127  L  G  A  R  A  S  P  P  R  S  G  V  S  L  A  R  P  A  P  G   146
                                               SCA2-A
601 TGTCCCCGCCCGGCGTGCGAGCCGGTGTATGGGCCCCTCACCATGTCGCTGAAGCCCCAG   660
147  C  P  R  P  A  C  E  P  V  Y  G  P  L  T  M  S  L  K  P  Q   166
661 CAGCAGCAGCAGCAGCAGCAGCAACAGCAGCAGCAACAGCAGCAGCAGCAGCAGCAGCAG   720
167  Q  Q  Q  Q  Q  Q  Q  Q  Q  Q  Q  Q  Q  Q  Q  Q  Q  Q  Q  Q   186
             SCA2-B
721 CAGCCGCCGCCCGCGGCTGCCAATGTCCGCAAGCCCGGCGGCAGCGGCCTTCTAGCGTCG   780
187  Q  P  P  P  A  A  A  N  V  R  K  P  G  G  S  G  L  L  A  S   206
781 CCCGCCGCCGCGCCTTCGCCGTCCTCGTCCTCGGTCTCCTCGTCCTCGGCCACGGCTCCC   840
207  P  A  A  A  P  S  P  S  S  S  S  V  S  S  S  S  A  T  A  P   226
841 TCCTCGGTGGTCGCGGCGACCTCCGGCGGCGGGAGGCCCGGCCTGGGCAGAGGTCGAAAC   900
227  S  S  V  V  A  A  T  S  G  G  R  P  G  L  G  R  G  R  N      246
901 AGTAACAAAGGACTGCCTCAGTCTACGATTTCTTTTGATGGAATCTATGCAAATATGAGG   960
247  S  N  K  G  L  P  Q  S  T  I  S  F  D  G  I  Y  A  N  M  R   266
961 ATGGTTCATATACTTACATCAGTTGTTGGCTCCAAATGTGAAGTACAAGTGAAAAATGGA  1020
267  M  V  H  I  L  T  S  V  V  G  S  K  C  E  V  Q  V  K  N  G   286
                                               SCA2-14B
1021 GGTATATATGAAGGAGTTTTTAAAACTTACAGTCCGAAGTGTGATTTGGTACTTGATGCC  1080
287  G  I  Y  E  G  V  F  K  T  Y  S  P  K  C  D  L  V  L  D  A   306
1081 GCACATGAGAAAAGTACAGAATCCAGTTCGGGGCCGAAACGTGAAGAAATAATGGAGAGT  1140
307  A  H  E  K  S  T  E  S  S  S  G  P  K  R  E  E  I  M  E  S   326
1141 ATTTTGTTCAAATGTTCAGACTTTGTTGTGGTACAGTTTAAAGATATGGACTCCAGTTAT  1200
327  I  L  F  K  C  S  D  F  V  V  Q  F  K  D  M  D  S  S  Y      346
1201 GCAAAAGAGATGCTTTTACTGACTCTGCTATCAGTGCTAAAGTGAATGGCGAACACAAA   1260
347  A  K  R  D  A  F  T  D  S  A  I  S  A  K  V  N  G  E  H  K   366
1261 GAGAAGGACCTGGAGCCCTGGGATGCAGGTGAACTCACAGCCAATGAGGAACTTGAGGCT  1320
367  E  K  D  L  E  P  W  D  A  G  E  L  T  A  N  E  E  L  E  A   386
1321 TTGGAAAATGACGTATCTAATGGATGGGATCCCAATGATATGTTTCGATATAATGAAGAA  1380
387  L  E  N  D  V  S  N  G  W  D  P  N  D  M  F  R  Y  N  E  E   406
1381 AATTATGGTGTAGTGTCTACGTATGATAGCAGTTTATCTTCGTATACAGTGCCCTTAGAA  1440
407  N  Y  G  V  V  S  T  Y  D  S  S  L  S  S  Y  T  V  P  L  E   426
1441 AGAGATAACTCAGAAGAATTTTTAAAACGGGAAGCAAGGGCAAACCAGTTAGCAGAAGAA  1500
427  R  D  N  S  E  E  F  L  K  R  E  A  R  A  N  Q  L  A  E  E   446
```

FIG. 6A

```
1501  ATTGAGTCAAGTGCCCAGTACAAAGCTCGAGTGGCCCTGGAAAATGATGATAGGAGTGAG  1560
447    I  E  S  S  A  Q  Y  K  A  R  V  A  L  E  N  D  D  R  S  E   466
1561  GAAGAAAAATACACAGCAGTTCAGAGAAATTCCAGTGAACGTGAGGGGCACAGCATAAAC  1620
467    E  E  K  Y  T  A  V  Q  R  N  S  S  E  R  E  G  H  S  I  N   486
1621  ACTAGGGAAAATAAATATATTCCTCCTGGACAAAGAAATAGAGAAGTCATATCCTGGGGA  1680
487    T  R  N  K  Y  I  P  P  G  Q  R  N  R  E  V  I  S  W  G      506
1681  AGTGGGAGACAGAATTCACCGCGTATGGGCCAGCCTGGATCGGGCTCCATGCCATCAAGA  1740
507    S  G  R  Q  N  S  P  R  M  G  Q  P  G  S  G  S  M  P  S  R   526
1741  TCCACTTCTCACACTTCAGATTTCAACCCGAATTCTGGTTCAGACCAAAGAGTAGTTAAT  1800
527    S  T  H  T  S  D  F  N  P  N  S  G  S  D  Q  R  V  V  N      546
1801  GGAGGTGTTCCCTGGCCATCGCCTTGCCCATCTCCTTCCTCTCGCCCACCTTCTCGCTAC  1860
547    G  G  V  P  W  P  S  P  C  P  S  P  S  S  R  P  P  S  R  Y   566
1861  CAGTCAGGTCCCAACTCTCTTCCACCTCGGGCAGCCACCCCTACACGGCCGCCCTCCAGG  1920
567    Q  S  G  P  N  S  L  P  P  R  A  A  T  P  T  R  P  P  S  R   586
1921  CCCCCCTCGCGGCCATCCAGACCCCCGTCTCACCCCTCTGCTCATGGTTCTCCAGCTCCT  1980
587    P  P  S  R  P  S  R  P  P  S  H  P  S  A  H  G  S  P  A  P   606
1981  GTCTCTACTATGCCTAAACGCATGTCTTCAGAAGGGCCTCCAAGGATGTCCCCAAAGGCC  2040
607    V  S  T  M  P  K  R  M  S  S  E  G  P  P  R  M  S  P  K  A   626
2041  CAGCGACATCCTCGAAATCACAGAGTTTCTGCTGGGAGGGGTTCCATATCCAGTGGCCTA  2100
627    Q  R  H  P  R  N  H  R  V  S  A  G  R  G  S  I  S  S  G  L   646
2101  GAATTTGTATCCGACAACCCACCCAGTGAAGCAGCTACTCCTCCAGTAGCAAGGACCAGT  2160
647    E  F  V  S  H  N  P  P  S  E  A  A  T  P  P  V  A  R  T  S   666
2161  CCCTCGGGGGGAACGTGGTCATCAGTGGTCAGTGGGGTTCCAAGATTATCCCCTAAAACT  2220
667    P  S  G  G  T  W  S  S  V  V  S  G  V  P  R  L  S  P  K  T   686
2221  CATAGACCCAGGTCTCCCAGACAGAACAGTATTGGAAATACCCCCAGTGGGCCAGTTCTT  2280
687    H  R  P  R  S  P  R  Q  N  S  I  G  N  T  P  S  G  P  V  L   706
2281  GCTTCTCCCCAAGCTGGTATTATTCCAACTGAAGCTGTTGCCATGCCTATTCCAGCTGCA  2340
707    A  S  P  Q  A  G  I  I  P  T  E  A  V  A  M  P  I  P  A  A   726
2341  TCTCCTACGCCTGCTAGTCCTGCATCGAACAGAGCTGTTACCCCTTCTAGTGAGGCTAAA  2400
727    S  P  T  P  A  S  P  A  S  N  R  A  V  T  P  S  S  E  A  K   746
2401  GATTCCAGGCTTCAAGATCAGAGGCAGAACTCTCCTGCAGGGAATAAAGAAAATATTAAA  2460
747    D  S  R  L  Q  D  Q  R  Q  N  S  P  A  G  N  K  E  N  I  K   766
2461  CCCAATGAAACATCACCTAGCTTCTCAAAAGCTGAAAACAAAGGTATATCACCAGTTGTT  2520
767    P  N  E  T  S  P  S  F  S  K  A  E  N  K  G  I  S  P  V  V   786
2521  TCTGAACATAGAAAACAGATTGATGATTTAAAGAAATTTAAGAATGATTTTAGGTTACAG  2580
787    S  E  H  R  K  Q  I  D  D  L  K  K  F  K  N  D  F  R  L  Q   806
2581  CCAAGTTCTACTTCTGAATCTATGGATCAACTACTAAACAAAAATAGAGAGGGAGAAAAA  2640
807    P  S  S  T  S  E  S  M  D  Q  L  L  N  K  N  R  E  G  E  K   826
2641  TCAAGAGATTTGATCAAAGACAAAATTGAACCAAGTGCTAAGGATTCTTTCATTGAAAAT  2700
827    S  R  D  L  I  K  D  K  I  E  P  S  A  K  D  S  F  I  E  N   846
2701  AGCAGCAGCAACTGTACCAGTGGCAGCAGCAAGCCGAATAGCCCCAGCATTTCCCCTTCA  2760
847    S  S  S  N  C  T  S  G  S  S  K  P  N  S  P  S  I  S  P  S   866
2761  ATACTTAGTAACACGGAGCACAAGAGGGGACCTGAGGTCACTTCCCAAGGGGTTCAGACT  2820
867    I  L  S  N  T  E  H  K  R  G  P  E  V  T  S  Q  G  V  Q  T   886
2821  TCCAGCCCAGCATGTAAACAAGAGAAAGACGATAAGGAAGAGAAGAAAGACGCAGCTGAG  2880
887    S  S  P  A  C  K  Q  E  K  D  D  K  E  E  K  K  D  A  A  E   906
2881  CAAGTTAGGAAATCAACATTGAATCCCAATGCAAAGGAGTTCAACCCACGTTCCTTCTCT  2940
907    Q  V  R  K  S  T  L  N  P  N  A  K  E  F  N  P  R  S  F  S   926
2941  CAGCCAAAGCCTTCTACTACCCCAACTTCACCTCGGCCTCAAGCACAACCTAGCCCATCT  3000
927    Q  P  K  P  S  T  T  P  T  S  P  R  P  Q  A  Q  P  S  P  S   946
3001  ATGGTGGGTCATCAACAGCCAACTCCAGTTTATACTCAGCCTGTTTGTTTTGCACCAAAT  3060
947    M  V  G  H  Q  Q  P  T  P  V  Y  T  Q  P  V  C  F  A  P  N   966
3061  ATGATGTATCCAGTCCCAGTGAGCCCAGGCGTGCAACCTTTATACCCAATACCTATGACG  3120
967    M  M  Y  P  V  P  V  S  P  G  V  Q  P  L  Y  P  I  P  M  T   986
```

FIG. 6B

```
3121  CCCATGCCAGTGAATCAAGCCAAGACATATAGAGCAGTACCAAATATGCCCCAACAGCGG  3180
 987   P  M  P  V  N  Q  A  K  T  Y  R  A  V  P  N  M  P  Q  Q  R   1006
3181  CAAGACCAGCATCATCAGAGTGCCATGATGCACCCAGCGTCAGCAGCGGGCCCACCGATT  3240
1007   Q  D  Q  H  H  Q  S  A  M  M  H  P  A  S  A  A  G  P  P  I   1026
3241  GCAGCCACCCCACCAGCTTACTCCACGCAATATGTTGCCTACAGTCCTCAGCAGTTCCCA  3300
1027   A  A  T  P  P  A  Y  S  T  Q  Y  V  A  Y  S  P  Q  Q  F  P   1046
3301  AATCAGCCCCTTGTTCAGCATGTGCCACATTATCAGTCTCAGCATCCTCATGTCTATAGT  3360
1047   N  Q  P  L  V  Q  H  V  P  H  Y  Q  S  Q  H  P  H  V  Y  S   1066
3361  CCTGTAATACAGGGTAATGCTAGAATGATGGCACCACCAACACACGCCCAGCCTGGTTTA  3420
1067   P  V  I  Q  G  N  A  R  M  M  A  P  P  T  H  A  Q  P  G  L   1086
3421  GTATCTTCTTCAGCAACTCAGTACGGGGCTCATGAGCAGACGCATGCGATGTATGCATGT  3480
1087   V  S  S  S  A  T  Q  Y  G  A  H  E  Q  T  H  A  M  Y  A  C   1106
3481  CCCAAATTACCATACAACAAGGAGACAAGCCCTTCTTTCTACTTTGCCATTTCCACGGGC  3540
1107   P  K  L  P  Y  N  K  E  T  S  P  S  F  Y  F  A  I  S  T  G   1126
3541  TCCCTTGCTCAGCAGTATGCGCACCCTAACGCTACCCTGCACCCACATACTCCACACCCT  3600
1127   S  L  A  Q  Q  Y  A  H  P  N  A  T  L  H  P  H  T  P  H  P   1146
3601  CAGCCTTCAGCTACCCCCACTGGACAGCAGCAAAGCCAACATGGTGGAAGTCATCCTGCA  3660
1147   Q  P  S  A  T  P  T  G  Q  Q  Q  S  Q  H  G  G  S  H  P  A   1166
3661  CCCAGTCCTGTTCAGCACCATCAGCACCAGGCCGCCCAGGCTCTCCATCTGGCCAGTCCA  3720
1167   P  S  P  V  Q  H  H  Q  H  Q  A  A  Q  A  L  H  L  A  S  P   1186
3721  CAGCAGCAGTCAGCCATTTACCACGCGGGGCTTGCGCCAACTCCACCCTCCATGACACCT  3780
1187   Q  Q  Q  S  A  I  Y  H  A  G  L  A  P  T  P  P  S  M  T  P   1206
3781  GCCTCCAACACGCAGTCGCCACAGAATAGTTTCCCAGCAGCACAACAGACTGTCTTTACG  3840
1207   A  S  N  T  Q  S  P  Q  N  S  F  P  A  A  Q  Q  T  V  F  T   1226
3841  ATCCATCCTTCTCACGTTCAGCCGGCGTATACCAACCCACCCCACATGGCCCACGTACCT  3900
1227   I  H  P  S  H  V  Q  P  A  Y  T  N  P  P  H  M  A  H  V  P   1246
3901  CAGGCTCATGTACAGTCAGGAATGGTTCCTTCTCATCCAACTGCCCATGCGCCAATGATG  3960
1247   Q  A  H  V  Q  S  G  M  V  P  S  H  P  T  A  H  A  P  M  M   1266
3961  CTAATGACGACACAGCCACCCGGCGGTCCCCAGGCCGCCCTCGCTCAAAGTGCACTACAG  4020
1267   L  M  T  T  Q  P  P  G  G  P  Q  A  A  L  A  Q  S  A  L  Q   1286
4021  CCCATTCCAGTCTCGACAACAGCGCATTTCCCCTATATGACGCACCCTTCAGTACAAGCC  4080
1287   P  I  P  V  S  T  T  A  H  F  P  Y  M  T  H  P  S  V  Q  A   1306
4081  CACCACCAACAGCAGTTGTAAGGCTGCCCTGGAGGAACCGAAAGGCCAAATTCCCTCCTC  4140
1307   H  H  Q  Q  Q  L  *                                           1326
4141  CCTTCTACTGCTTCTACCAACTGGAAGCACAGAAAACTAGAATTTCATTTATTTTGTTTT  4200
4201  TAAAATATATATGTTGATTTCTTGTAACATCCAATAGGAATGCTAACAGTTCACTTGCAG  4260
4261  TGGAAGATACTTGGACCGAGTAGAGGCATTTAGGAACTTGGGGGCTATTCCATAATTCCA  4320
4321  TATGCTGTTTCAGAGTCCCGCAGGTACCCCAGCTCTGCTTGCCGAAACTGGAAGTTATTT  4380
4381  ATTTTTTAATAACCCTTGAAAGTCATGAACACATCAGCTAGCAAAAGAAGTAACAAGAGT  4440
4441  GATTCTTGCTGCTATTACTGCTAAAAAAAAAAAAAAAAAAA  4481
```

FIG. 6C

```
                   1                                                        50
Ataxin-2           VYGPLTMSLK  PQQQQQQQQQ  QQQQQQQQQQ  QQQPPPAAAN  VRKPGGSGLL
Mouse Ataxin-2     HEGPLTMSLK  PQPQ......  ..........  ....PPAPAT  GRKPGG.GLL
A2RP               ........LA  PQPPPPQQHQ  ER........  ..........  ..........
    Consensus      --------L-  PQ--------  ----------  ----------  ----------

51                                                       100
Ataxin-2           ASPAAAPSPS  SSSVSSSSAT  APSSVVA...  ATSGGGRPGL  GRGRNSNKGL
Mouse Ataxin-2     SSPGAAP.AS  AAVTSASVVP  APAAPVASSS  AAAGGGRPGL  GRGRNSSKGL
A2RP               ..PGAAAIGS  A.........  ..........  ..........  .RGQSTGKGP
    Consensus      --P-AA---S  ----------  ----------  ----------  -RG----KG- 101                                                      150
Ataxin-2           PQSTISFDGI  YANMRMVHIL  TSVVGSKCEV  QVKNGGIYEG  VFKTYSPKCD
Mouse Ataxin-2     PQPTISFDGI  YANVRMVHIL  TSVVGSKCEV  QVKNGGIYEG  VFKTYSPKCD
A2RP               PQSPV.FEGV  YNNSRMLHFL  TAVVGSTCDV  KVKNGTTYEG  IFKTLSSKFE
    Consensus      PQ-----F-G-  Y-N-RM-H-L  T-VVGS-C-V  -VKNG--YEG  -FKT-S-K--

151                                                      200
Ataxin-2           LVLDAAHEKS  TESSSGPKRE  EIMESILFKC  SDFVVVQFKD  MDSSYAKRDA
Mouse Ataxin-2     LVLDAAHEKS  TESSSGPKRE  EIMESVLFKC  SDFVVVQFKD  TDSSYARRDA
A2RP               LAVDAVHRKA  SEPAGGPRRE  DIVDTMVFKP  SDVMLVHFRN  VDFNYATKDK
    Consensus      L--DA-H-K-  -E---GP-RE  -I-----FK-  SD---V-F--  -D--YA--D-

201                                                      250
Ataxin-2           FTDSAIS..A  KVNGEHKEKD  LEPWDAGELT  ANEELEALEN  DVSNGWDPND
Mouse Ataxin-2     FTDSALS..A  KVNGEHKEKD  LEPWDAGELT  ASEELE.LEN  DVSNGWDPND
A2RP               FTDSAIAMNS  KVNGEHKEKV  LQRWEGGD.S  NSDDYD.LES  DMSNGWDPNE
    Consensus      FTDSA-----  KVNGEHKEK-  L--W--G---  -------LE-  D-SNGWDPN- 251                                                      300
Ataxin-2           MFRYNEENYG  VVSTYDSSLS  SYTVPLERDN  SEEFLKREAR  ANQLAEEIES
Mouse Ataxin-2     MFRYNEENYG  VVSTYDSSLS  SYTVPLERDN  SEEFLKREAR  ANQLAEEIES
A2RP               MFKFNEENYG  VKTTYDSSLS  SYTVPLEKDN  SEEFRQRELR  AAQLAREIES
    Consensus      MF--NEENYG  V--TYDSSLS  SYTVPLE-DN  SEEF--RE-R  A-QLA-EIES 301                                                      350
Ataxin-2           SAQYKARVAL  ENDD.RSEEE  KYTAVQRNSS  EREGHSINTR  ENKYIPPGQR
Mouse Ataxin-2     SAQYKARVAL  ENDD.RSEEE  KYTAVQRNCS  DREGHGPNTR  DNKYIPPGQR
A2RP               SPQYRLRIAM  ENDDGRTEEE  KHSAVQRQGS  GRESPSLASR  EGKYIP....
    Consensus      S-QY--R-A-  ENDD-R-EEE  K--AVQR--S  -RE------R  --KYIP----

351
Ataxin-2           NR
Mouse Ataxin-2     NR
A2RP               ..
    Consensus      --
```

FIG. 7

METHODS OF DETECTING SPINOCEREBELLAR ATAXIA-2 NUCLEIC ACIDS

This application is a division of U.S. Patent Application Ser. No. 08/727,084, filed Oct. 8, 1996, now abandoned, which is incorporated herein by reference, and which further claims the benefit of U.S. patent application Ser. No. 60/022,207, filed Jul. 19, 1996, now abandoned, and U.S. patent application Ser. No. 60/017,388, filed May 8, 1996, now abandoned.

BACKGROUND OF THE INVENTION

Disorders of the cerebellum and its connections are a major cause of neurologic morbidity and mortality. One of the cardinal features of lesions in these pathways is ataxia or incoordination of movements and gait. Although some of the lesions have obvious etiologies such as trauma, strokes or tumors, the etiology of many ataxias has remained difficult to define and is due to metabolic deficiencies, remote effects of cancer or genetic causes. Hereditary spinocerebellar degenerations have a prevalence of 7–20 cases per 100,000 (Filla et al., *J. of Neurology* 239(6):351–353 (1992); Polo et al., *Brain* 114 (pt2):855–866 (1991)) which equals the estimates for the prevalence of multiple sclerosis in the United States Based on clinical analysis and genetic inheritance patterns several forms of ataxias are now recognized. Among the genetic causes of ataxic disorders, the autosomal dominant spinocerebellar ataxias (SCAs) have been the most difficult to classify and until recently no clues to their cause existed.

The SCAs are progressive degenerative neurological diseases of the nervous system characterized by a progressive degeneration of neurons of the cerebellar cortex. Degeneration is also seen in the deep cerebellar nuclei, brain stem, and spinal cord. Clinically, affected individuals suffer from severe ataxia and dysarthria, as well as from variable degrees of motor disturbance and neuropathy. The disease usually results in complete disability and eventually in death 10 to 30 years after onset of symptoms. The genes for SCA types 1 and 3 have been identified. Both contain CAG DNA repeats that cause the disease when expanded. However, little is known how CAG repeat expansion and consequent elongation of polyglutamine tracts translate into neurodegeneration. The identification of the SCA2 gene would provide the opportunity to study this phenomenon in a new protein system.

The significance of identifying ataxia genes goes beyond improved diagnosis for individuals, the possibility of prenatal/presymptomatic diagnosis or better classification of ataxias. Most of the genes associated with repeat expansions in the coding region including the genes for SCA1 and SCA3 are genes that show no homology to known genes. Thus, isolation of these genes will likely point to pathways leading to late-onset neurodegeneration that are novel and may have importance for other neurodegenerative diseases.

For example, it has been suggested that CAG expansion may result in increased transglutamination of proteins, a process that has also been implicated in Alzheimer's disease. The ataxias in particular offer the unique opportunity to study how different genes may either independently or through conjoined action in the same pathway produce relatively similar phenotypes in humans. Therefore, it may be possible to examine the interaction of these genes on age of onset and phenotype, and explain that part of phenotypic variability that is not explained by determining repeat expansion in the mutant allele. Cosmids and YACs have been the main tools for generating contig maps of chromosomal regions and the entire genome, respectively. Recently, novel cloning vectors (reviewed in Ioannou et al., *Nat. Genet.* 6:84–89 (1994)) have been developed that may be more stable than cosmids, while being considerable larger.

Several systems of classification have been proposed for the SCAs based on pathological, clinical or genetic criteria. However, these attempts have been hampered by the extreme variability of disease onset and clinical features within and between families. Among the dominant ataxias only Machado-Joseph disease (MJD) has been clinically defined as a separate disease based on the prominence of basal ganglia involvement. However, since phenotypic variability is remarkable in MJD pedigrees, the assignment of individual cases or small families to this category is difficult. Indeed, after identification of the MJD locus (SCA3) it has become apparent that families with a phenotype not typical of MJD, but resembling SCAs are linked to the same locus as SCA3 families.

The advent of genetic linkage analysis provided a novel means to approach classification of the SCAs. Since the late 70's it was recognized that some SCA pedigrees appeared to show linkage to the HLA locus on CHR6, while others did not. Later this locus, now called SCA1, was further defined using RFLP and microsatellite markers and was mapped centromeric to the HLA locus. After the establishment of flanking markers for the SCA1 gene it became rapidly apparent that many—if not the majority—of SCA families did not show linkage to the SCA1 locus. Recently, a second SCA locus was identified on CHR12 using a large pedigree of Cuban descent (Gispert et al., *Nat. Genet.* 4:295–299 (1993)) and in a pedigree of Southern Italian origin (Pulst et al., *Nat. Genet.* 5:8–10 (1993)). At the same time a third locus for Machado-Joseph disease and other pedigrees with an SCA phenotype was identified on CHR14 (Takiyama et al, *Nat. Genet.* 4:300–304 (1993)). Recently, SCA4 was mapped to CHR16 and SCA5 to CHR11 (Ranum et al., *Nat. Genet.* 8:N3:280–284 (1994)).

Two of the SCA genes have been identified, one by a positional cloning approach, the other by a cDNA based approach. The SCA1 gene was identified by screening a cosmid contig covering the region between the two flanking markers D6S274 and D6S89 for cosmids containing CAG repeats. A CAG repeat was isolated, and shown to be expanded in affected individuals (Orr et al., *Nat. Genet.* 4:221–226 (1993); see Table 1). The number of CAG repeats are inversely correlated with the age of onset. Recently, the complete coding sequence for the SCA1 gene has been determined. The gene does not appear to be homologous to other known genes. Despite the tissue specific effects of the mutation, SCA1 transcripts are ubiquitously expressed. By RT-PCR analysis, normal and mutated transcripts are found in tissues indicating that repeat expansion does not interfere with transcription.

The SCA3 or MJD gene was identified after several CAG containing cDNA clones had been isolated from a brain cDNA library (Kawaguchi et al., Nat. Genet. 8:221–227 (1994)). One of these mapped to CHR 14q32.1, the region previously identified by genetic linkage analysis to contain the SCA3 gene. The CAG repeat was expanded in affected individuals, but appears to show greater meiotic stability than other CAG repeats. The SCA3 gene has no homology to other known genes or motif structures, but related sequences were identified on CHR 8q23, 14q21, and Xp22.1.

Although not an SCA gene in the strict sense, CAG expansion in the gene causing dentatorubral-pallidoluysian atrophy (DRPLA) may also lead to degeneration of cerebellar neurons. This gene was identified by searching published brain cDNA sequences for the presence of CAG repeats. A cDNA mapped to CHR12p was found to harbor a CAG repeat which was expanded in DRPLA patients (Koide et al., *Nat. Genet.* 6:9–13 (1994); Nagafuchi et al., *Nat. Genet.* 6:14–18 (1994)). The gene which has no known homologies is ubiquitously expressed. SCA families linked to markers on CHR 12 have been described in several ethnic backgrounds. The largest ones are of Cuban ancestry (H pedigree), French-Canadian and Austrian ancestry (SAK and GK pedigrees, Lopes-Cendes et al., *Am. J. Hum. Genet.* 54:774–781 (1994)) and Italian descent (FS pedigree, Pulst et al., (1993)). A smaller Tunisian pedigree has been described as well (Belal et al., *Neurology* 44:1423–1426 (1994)). Although all pedigrees have cases with early onset in recent generations, a formal age of onset analysis has only been performed for the FS pedigree. This analysis indicated clear evidence of anticipation (Pulst et al., (1993)).

The phenomenon of unstable DNA repeats raises many fascinating issues. For example, in 1991, La Spada et al. identified a polymorphic CAG repeat in the androgen receptor gene on the X chromosome that was greatly expanded in individuals with spinobulbar muscular atrophy (SBMA, Kennedy syndrome). In short succession, a total of ten diseases were found to be caused by trinucleotide repeat (TNR) expansion (Table 1). Although several unifying concepts emerge from the comparison of diseases caused by TNR expansion, important differences can be recognized as well.

Common to all diseases is a highly polymorphic number of repeats on normal chromosomes. If the repeat number reaches allele sizes in between normal and disease alleles—termed premutations—the repeat becomes unstable and may expand to the size associated with the disease state. Large number repeats have the tendency to expand further, although decreases in size are occasionally seen (Bruner et al., *New Engl. J. Med.* 328:476–480 (1993); reviewed in Brook, *Nat. Genet.* 3:279–152 (1993); Mandel, *Nat. Genet.* 4:8–9 (1993)).

TABLE 1

Characteristics of diseases caused by TNR expansion

| Disease | Type of repeat | Location of repeat | Number of repeats in normal alleles | in disease alleles |
|---|---|---|---|---|
| Fragile X syndrome | CGG | 5' untr. | 5–54 | 200–200 |
| FRAXE | GCC | unknown | 6–25 | 200–80 |
| FRAXF | GCC | unknown | 6–29 | 300–500 |
| FRA16A | GCC | unknown | 16–49 | 1000–20000 |
| Myotonic dystrophy | CTG | 3' untr. | 5–35 | 100–200 |
| SBMA | CAG | coding | 11–31 | 40–62 |
| Huntington disease | CAG | coding | 15–38 | 38–120 |
| CA 1 | CAG | coding | 25–36 | 43–81 |
| DRPLA | CAG | coding | 7–26 | 49–75 |
| MJD (SCA3) | CAG | coding | 13–36 | 68–79 |

TNR expansion may be a common form of human mutagenesis. Especially if expansion is not restricted to pure CAG and CCG repeats, the number of genes predisposed to expansion may be quite large. Three diseases with cerebellar degeneration, SCA1, DRPLA, and SCA3 are caused by expansion of a CAG repeat. In these diseases clear evidence of anticipation was lacking, although very early onset cases in some families had raised this question. However, as described in Pulst et al. (1993) strong evidence for anticipation was identified in the FS pedigree with SCA2. Thus, there is a need in the art to identify the location and nucleic acid structure of the SCA2 gene.

SUMMARY OF THE INVENTION

The present invention provides isolated nucleic acids encoding the human SCA2 protein and isolated proteins encoded thereby. Further provided are vectors containing invention nucleic acids, probes that hybridize thereto, host cells transformed therewith, antisense oligonucleotides thereto and compositions containing, antibodies that specifically bind to invention polypeptides and compositions containing, as well as transgenic non-human mammals that express the invention protein. In addition, methods for diagnosing spinocerebellar Ataxia Type 2, or a predisposition thereto, are provided.

BRIEF DESCRIPTION OF THE FIGURES

FIG. 2 shows the nucleic acid sequence (SEQ ID NO:1) of plasmid PL65I22B for genomic DNA encoding the expansion of the CAG repeat in individuals with SCA2. Nucleotides 1–499 of FIG. 2 correspond to cDNA nucleotides 392–890 of FIG. 6 (SEQ ID NO:2). The locations of primers SCA2-A and SCA2-B are indicated by arrows. The location of a predicted splice site is indicated by a vertical arrow between nucleotides 499 and 500 (also compare with FIG. 6).

FIG. 6 shows the composite cDNA sequence (SEQ ID NO:2) obtained from assembly of the partially overlapping cDNA clones shown in FIG. 5. The predicted SCA2 protein product (SEQ ID NO:3) is shown below the DNA sequence. The stop codon for the SCA2 cDNA is indicated by *. The locations of primers SCA2-A (SEQ ID NO:6), SCA2-B (SEQ ID NO:7) and SCA2–B14(SEQ ID NO:15) are indicated by horizontal arrows. The splice site between primers SCA2-B and SCA2–B14 is indicated by a vertical arrow.

FIG. 7 shows a partial amino acid sequence alignment comparison of ataxin-2 protein, the ataxin-2 related protein (A2RP), and the mouse SCA2 homologue in the region of strongest homology. Codon 1 corresponds to codon 155 in FIG. 6 (SEQ ID NO:3).

DETAILED DESCRIPTION OF THE INVENTION

Figure 1:
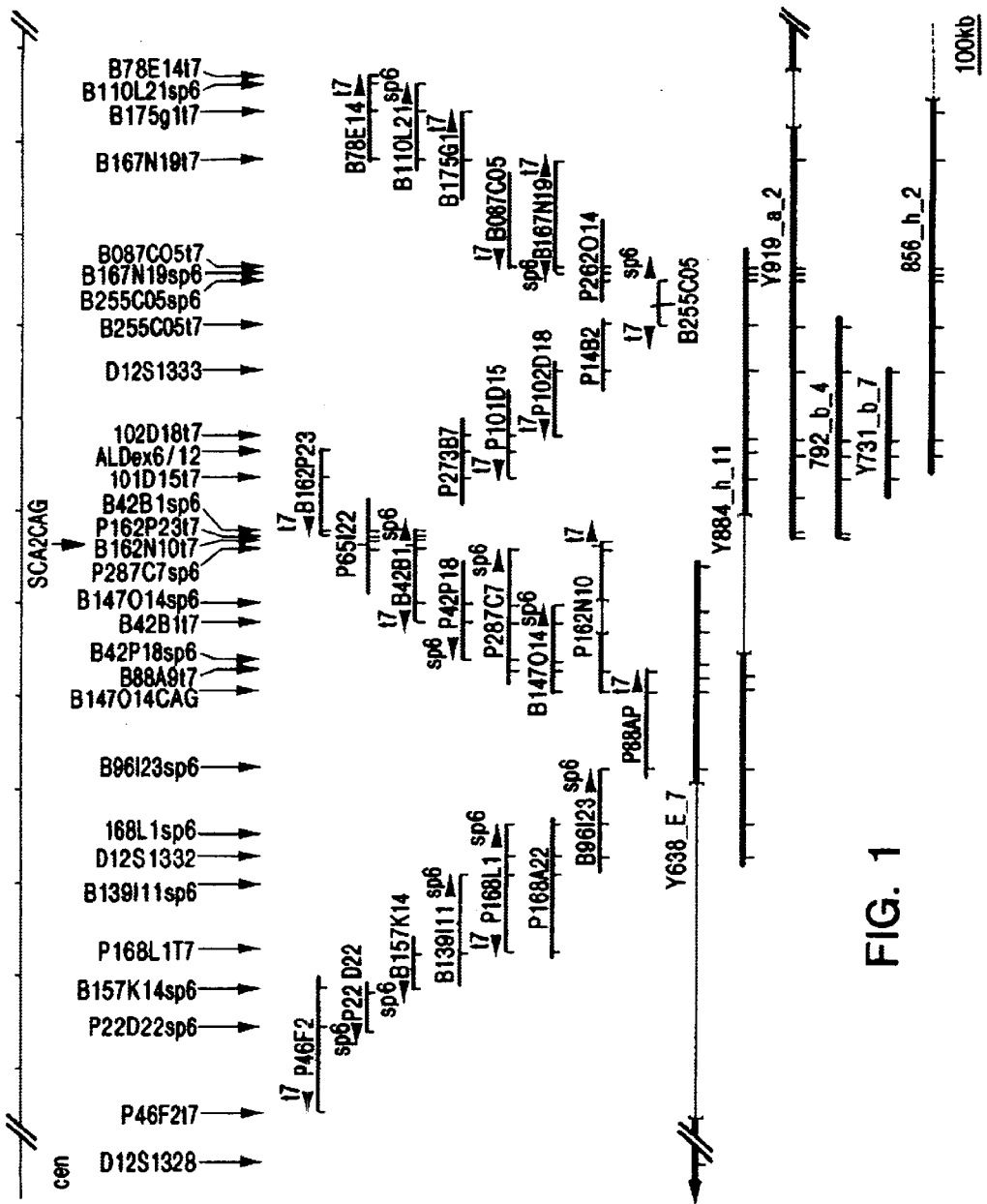
FIG. 1 shows a physical map of the SCA2 region. The location of D12S1328 centromeric and D12S1329 telomeric of the contig are indicated. As indicated by double forward slashes, the map is not drawn to scale between D12S1328 and P46F2t7, and between B78E14t7 and D12S1329. YAC, PAC and BAC clones are prefixed with 'Y', 'P', and 'B' respectively. Clones positive for a specific STS by PCR analysis are indicated by vertical lines. Solid arrows indicate end-STSs from the clone under the symbol. Sizes of all clones are shown to scale. The chimeric part of YAC clone 856__h$_2$(1,100 kb) is indicated by a dashed arrow. Interstitial deletions in YACs or PACs are indicated by thin lines in brackets. The extent of the deletion in YAC Y638 .e.7 is not precisely known.

The hereditary ataxias are a complex group of neurodegenerative disorders all characterized by varying abnormalities of balance attributed to dysfunction or pathology of the cerebellum and cerebellar pathways. In many of these disorders, dysfunction or structural abnormalities extend beyond the cerebellum, and may involve basal ganglia function, oculo-motor disorders and neuropathy. Among the inherited ataxias, the classification of dominant adult onset ataxias is particularly controversial with regard to nomenclature, associated findings and pathology. The dominant spinocerebellar ataxias (SCAs) represent a phenotypically heterogeneous group of disorders with a prevalence of familial cases of approximately 1 per 100,000. This group of disorders is also designated as olivo-ponto-cerebellar atrophies (OPCAs), although this term is too restrictive a pathological label.

The high phenotypic variability within single SCA pedigrees has made clinical classification of different forms of ataxia difficult. The gene causing SCA1 has been identified on CHR 6p and the SCA3 gene has been identified on CHR 14q. These diseases are caused by expansion of a CAG repeat in the coding region of the genes. However, many SCA pedigrees do not show linkage to CHR 6p or CHR 14q, confirming the presence of non-allelic heterogeneity. Subsequent genetic linkage studies have led to the identification of SCA loci on CHR12 and some families do not show linkage to either of the above three chromosomal regions.

Described in the instant specification is the construction of the BAC (Bacterial Artificial Chromosome) Shizuya et al., *Proc. Natl. Acad. Sci. USA* 89:8794–8797 (1992) contig and PAC (P1 Artificial Chromosome) of the SCA2 region and the isolation of a novel SCA2 gene from this contiguous map unit using a technique that screens for the presence of DNA trinucleotide repeats.

Sequence analysis of the DNA sequence flanking the CAG repeat revealed an open reading frame of 317 base pairs (FIG. 2). A homology search of the amino acid sequence of this open reading frame (ORF) with genes registered in Genbank/EMBL and search of the TIGR database showed no homologous proteins or homologous genomic DNA sequences. Using reverse-transcribed PCR (polymerase chain reaction) with primers SCA1-A and SCA1-B, the genomic sequence containing the CAG repeat was shown to be expressed into mRNA. Subsequently, cDNA encoding human and mouse SCA2 has been isolated as described hereinafter in Examples 4 and 7, respectively.

Accordingly, the present invention provides isolated nucleic acids, which encode a novel mammalian SCA2 protein, and fragments thereof. Such nucleic acids can be obtained, for example, from human chromosome 12, specifically at the q24.1 locus, which is the site of mutation(s) that cause SCA2.

The term "nucleic acids" (also referred to as polynucleotides) encompasses RNA as well as single and double-stranded DNA and cDNA. As used herein, the phrase "isolated" means a nucleic acid that is in a form that does not occur in nature. One means of isolating a nucleic acid encoding an SCA2 polypeptide is to probe a mammalian genomic library with a natural or artificially designed DNA probe using methods well known in the art. DNA probes derived from the SCA2 gene are particularly useful for this purpose. DNA and cDNA molecules that encode SCA2 polypeptides can be used to obtain complementary genomic DNA, cDNA or RNA from human, mammalian (e.g., mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding an SCA2 polypeptide. Such invention nucleic acids may include, but are not limited to, nucleic acids having substantially the same nucleotide sequence as nucleotides 163–4098 set forth in SEQ ID NO:2 (FIG. 6), or at least nucleotides 163–657 or nucleotides 724–4098 of SEQ ID NO:2; or SEQ ID NO:4. In a preferred embodiment, invention nucleic acids include the same nucleotide sequence as nucleotides 163–4098 of SEQ ID NO:2, or include the same nucleotide sequence as SEQ ID NO:4.

As employed herein, the phrase "substantially the same nucleotide sequence" refers to DNA having sufficient homology to the reference polynucleotide, such that it will hybridize to the reference nucleotide under typical moderate stringency conditions. In one embodiment, nucleic acid molecules having substantially the same nucleotide sequence as the reference nucleotide sequence encodes substantially the same amino acid sequence as that of either SEQ ID NO:3, or SEQ ID NO:5. In another embodiment, DNA having "substantially the same nucleotide sequence" as the reference nucleotide sequence has at least 60% homology with respect to the reference nucleotide sequence. DNA having at least 70%, more preferably 80%, yet more preferably 90%, homology to the reference nucleotide sequence is preferred.

This invention also encompasses nucleic acids which differ from the nucleic acids shown in SEQ ID NO:1, SEQ ID NO:2, or SEQ ID NO:4, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding SCA2 polypeptides that, by virtue of the degeneracy of the genetic code, do not necessarily hybridize to the invention nucleic acids under specified hybridization conditions. Preferred nucleic acids encoding the invention polypeptide are comprised of nucleotides that encode substantially the same amino acid sequence set forth in SEQ ID NO:3 (FIG. 6), or SEQ ID NO:5.

As employed herein, the term "substantially the same amino acid sequence" refers to amino acid sequences having at least about 70% identity with respect to the reference amino acid sequence, and retaining comparable functional and biological properties characteristic of the protein defined by the reference amino acid sequence. Preferably, proteins having "substantially the same amino acid sequence" will have at least about 80%, more preferably 90% amino acid identity with respect to the reference amino acid sequence (SEQ ID NO:3 or SEQ ID NO:5); with greater than about 95% amino acid sequence identity being especially preferred.

Alternatively, preferred nucleic acids encoding the invention polypeptide(s) hybridize under moderately stringent, preferably high stringency, conditions to substantially the entire sequence, or substantial portions (i.e., typically at least 15–30 nucleotides) of the nucleic acid sequence set forth in SEQ ID NO:1, SEQ ID NO:2 (FIG. 6) or SEQ ID NO:4.

Stringency of hybridization, as used herein, refers to conditions under which polynucleotide hybrids are stable. As known to those of skill in the art, the stability of hybrids is a function of sodium ion concentration and temperature (See, for example, Sambrook et al., *Molecular Cloning: A Laboratory Manual* 2d Ed. (Cold Spring Harbor Laboratory, (1989); incorporated herein by reference). Stringency levels used to hybridize a given probe with target-DNA can be readily varied by those of skill in the art.

As used herein, the phrase "moderately stringent" hybridization refers to conditions that permit target-DNA to bind a complementary nucleic acid that has about 60%, preferably about 75%, more preferably about 85%, homology (i.e., identity) to the target DNA; with greater than about 90% homology to target-DNA being especially preferred. Preferably, moderately stringent conditions are conditions equivalent to hybridization in 50% formamide, 5× Denhart's solution, 5× SSPE, 0.2% SDS at 42° C., followed by washing in 0.2× SSPE, 0.2% SDS, at 65° C. Denhart's solution and SSPE (see, e.g., Sambrook et al., *Molecular Cloning, A Laboratory Manual,* Cold Spring Harbor Laboratory Press, (1989)) are well known to those of skill in the art as are other suitable hybridization buffers.

Also provided are isolated SCA2 peptides, polypeptides(s) and/or protein(s), or fragments thereof, encoded by the invention nucleic acids.

As used herein, the term "isolated" means a protein molecule free of cellular components and/or contaminants normally associated with a native in vivo environment. Invention polypeptides and/or proteins include any isolated natural occurring allelic variant, as well as recombinant forms thereof. The SCA2 polypeptides can be isolated using various methods well known to a person of skill in the art. The methods available for the isolation and purification of invention proteins include, precipitation, gel filtration, ion-exchange, reverse-phase and affinity chromatography. Other well-known methods are described in Deutscher et al., *Guide to Protein Purification: Methods in Enzymology* Vol. 182, (Academic Press, (1990)), which is incorporated herein by reference. Alternatively, the isolated polypeptides of the present invention can be obtained using well-known recombinant methods as described, for example, in Sambrook et al., supra, 1989).

An example of the means for preparing the invention polypeptide(s) is to express nucleic acids encoding the SCA2 in a suitable host cell, such as a bacterial cell, a yeast cell, an amphibian cell (i.e., oocyte), or a mammalian cell, using methods well known in the art, and recovering the expressed polypeptide, again using well-known methods. Invention polypeptides can be isolated directly from cells that have been transformed with expression vectors, described below in more detail. The invention polypeptide, biologically active fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

As used herein, the phrase "SCA2" refers to substantially pure native SCA2 protein, or recombinantly expressed/produced (i.e., isolated or substantially pure) proteins, including variants thereof encoded by mRNA generated by alternative splicing of a primary transcript, and further including fragments thereof which retain native biological activity. Preferred invention polypeptides are those that contain substantially the same amino acid sequence set forth in SEQ ID NO:3 (FIG. 6), or at least amino acids 1–165 or amino acids 188–1312 of SEQ ID NO:3, or include substantially the same amino acid sequence set forth in SEQ ID NO:5. As used herein, the phrase "functional polypeptide" means a SCA2 that can produce an anti-SCA2 antibody that binds to the native SCA2 protein or to the amino acid sequence set forth in SEQ ID NO:3 (FIG. 6), or SEQ ID NO:5. In a preferred embodiment, invention polypeptides include the same amino acid sequence as set forth in SEQ ID NO:3 or SEQ ID NO:5.

Modification of the invention nucleic acids, polypeptides or proteins with the following phrases: "recombinantly expressed/produced", "isolated", or "substantially pure", encompasses nucleic acids, peptides, polypeptides or proteins that have been produced in such form by the hand of man, and are thus separated from their native in vivo cellular environment. As a result of this human intervention, the recombinant nucleic acids, polypeptides and proteins of the invention are useful in ways that the corresponding naturally occurring molecules are not, such as identification of selective drugs or compounds.

Sequences having "substantially the same sequence" homology are intended to refer to nucleotide sequences that share at least about 75%, preferably about 80%, yet more preferably about 90% identity with invention nucleic acids; and amino acid sequences that typically share at least about 75%, preferably about 85%, yet more preferably about 95% amino acid identity with invention polypeptides. It is recognized, however, that polypeptides or nucleic acids containing less than the above-described levels of homology arising as splice variants or that are modified by conservative amino acid substitutions, or by substitution of degenerate codons are also encompassed within the scope of the present invention.

The present invention provides the isolated polynucleotide encoding SCA2 operatively linked to a promoter of RNA transcription, as well as other regulatory sequences. As used herein, the phrase "operatively linked" refers to the functional relationship of the polynucleotide with regulatory and effector sequences of nucleotides, such as promoters, enhancers, transcriptional and translational stop sites, and other signal sequences. For example, operative linkage of a polynucleotide to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide.

Promoter regions include specific sequences that are sufficient for RNA polymerase recognition, binding and transcription initiation. Additionally, promoter regions include sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, and the like.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. (See, for example, Kozak, *J. Biol. Chem.* 266:19867 (1991)). Similarly, alternative codons, encoding the same amino acid, can be substituted for coding sequences of the SCA2 polypeptide in order to enhance transcription (e.g., the codon preference of the host cell can be adopted, the presence of G-C rich domains can be reduced, and the like).

Also provided are vectors comprising invention nucleic acids. Examples of vectors are viruses, such as baculoviruses and retroviruses, bacteriophages, cosmids, plasmids and other recombination vehicles typically used in the art. Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA.

Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

Further provided are vectors comprising nucleic acids encoding SCA2 polypeptides, adapted for expression in a bacterial cell, a yeast cell, an amphibian cell (i.e., oocyte), a mammalian cell and other animal cells. The vectors additionally comprise the regulatory elements necessary for expression of the nucleic acid in the bacterial, yeast, amphibian, mammalian or animal cells so located relative to the nucleic acid encoding SCA2 polypeptide as to permit expression thereof.

As used herein, "expression" refers to the process by which nucleic acids are transcribed into mRNA and translated into peptides, polypeptides, or proteins. If the nucleic acid is derived from genomic DNA, expression may include splicing of the mRNA, if an appropriate eucaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al. supra) . Similarly, a eucaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general. Expression vectors are useful to produce cells that express the invention polypeptide.

The present invention provides transformed host cells that recombinantly express SCA2 polypeptides. An example of a transformed host cell is a mammalian cell comprising a plasmid adapted for expression in a mammalian cell. The plasmid contains nucleic acid encoding an SCA2 polypeptide and the regulatory elements necessary for expression of invention proteins. Various mammalian cells may be utilized as hosts, including, for example, mouse fibroblast cell NIH3T3, CHO cells, HeLa cells, Ltk- cells, etc. Expression plasmids such as those described supra can be used to transfect mammalian cells by methods well known in the art such as, for example, calcium phosphate precipitation, DEAE-dextran, electroporation, microinjection or lipofection.

The present invention provides nucleic acid probes comprising nucleotide sequences capable of specifically hybridizing with sequences included within nucleic acids encoding SCA2 polypeptides, for example, a coding sequence included within the nucleotide sequence shown in SEQ ID NO:2 (FIG. 6), or SEQ ID NO:4. In a preferred embodiment, the probe is derived from the nucleic acid sequence set forth in SEQ ID NO:2, or at least nucleotides 163–657 or nucleotides 724–4098 of SEQ ID NO:2; or SEQ ID NO:4. Preferred regions from which to construct probes include 5' and/or 3' coding sequences, sequences within the ORF, and the like. Full-length or fragments of cDNA clones encoding SCA2 can also be used as probes for the detection and isolation of related genes. As used herein, an invention "probe" or invention oligonucleotide is a single-stranded DNA or RNA that has a sequence of nucleotides that includes at least about 15 contiguous bases up to the full length coding region of SEQ ID NO:2 or SEQ ID NO:4. Preferably an invention probe is at least about 30 contiguous bases, more preferably at least about 50, yet more preferably at least about 100, with about 300 contiguous bases up to the full length coding region of SEQ ID NO:2 and SEQ ID NO:4 being especially preferred. When fragments are used as probes, preferably the cDNA sequences will be from the carboxyl end-encoding portion of the cDNA, and most preferably will include predicted transmembrane domain-encoding portions of the cDNA sequence. Transmembrane domain regions can be predicted based on hydropathy analysis of the deduced amino acid sequence using, for example, the method of Kyte and Doolittle, *J. Mol. Biol.* 157:105 (1982).

As used herein, the phrase "specifically hybridizing" encompasses the ability of a polynucleotide to recognize a sequence of nucleic acids that are complementary thereto and to form double-helical segments via hydrogen bonding between complementary base pairs. Nucleic acid probe technology is well known to those skilled in the art who will readily appreciate that such probes may vary greatly in length and may be labeled with a detectable agent, such as a radioisotope, a fluorescent dye, and the like, to facilitate detection of the probe. Invention probes are useful to detect the presence of nucleic acids encoding the SCA2 polypeptide. For example, the probes can be used for in situ hybridizations in order to locate biological tissues in which the invention gene is expressed. Additionally, synthesized oligonucleotides complementary to the nucleic acids of a nucleotide sequence encoding SCA2 polypeptide are useful as probes for detecting the invention genes, their associated mRNA, or for the isolation of related genes using homology screening of genomic or cDNA libraries, or by using amplification techniques well known to one of skill in the art.

Also provided are antisense oligonucleotides having a sequence capable of binding specifically with any portion of an mRNA that encodes SCA2 polypeptides so as to prevent or inhibit translation of the mRNA. The antisense oligonucleotide may have a sequence capable of binding specifically with any portion of the sequence of the cDNA encoding SCA2 polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense oligonucleotide is an antisense oligonucleotide comprising chemical analogs of nucleotides.

Compositions comprising an amount of the antisense oligonucleotide, described above, effective to reduce expression of SCA2 polypeptides by passing through a cell membrane and binding specifically with mRNA encoding SCA2 polypeptides so as to prevent translation and an acceptable hydrophobic carrier capable of passing through a cell membrane are also provided herein. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense oligonucleotide compositions are useful to inhibit translation of mRNA encoding invention polypeptides. Synthetic oligonucleotides, or other antisense chemical structures are designed to bind to mRNA encoding SCA2 polypeptides and inhibit translation of mRNA and are useful as compositions to inhibit expression of SCA2 associated genes in a tissue sample or in a subject.

In accordance with another embodiment of the invention, kits for detecting mutations and aneuploidies in chromosome 12 at locus q24.1 comprising at least one invention probe or antisense nucleotide.

The present invention provides means to modulate levels of expression of SCA2 polypeptides by employing synthetic antisense oligonucleotide compositions (hereinafter SAOC) which inhibit translation of mRNA encoding these polypeptides. Synthetic oligonucleotides, or other antisense chemical structures designed to recognize and selectively bind to mRNA, are constructed to be complementary to portions of the SCA2 coding strand or nucleotide sequences shown in SEQ ID NO:2, or SEQ ID NO:4. The SAOC is designed to be stable in the blood stream for administration to a subject by injection, or in laboratory cell culture conditions. The SAOC is designed to be capable of passing through the cell membrane in order to enter the cytoplasm of the cell by virtue of physical and chemical properties of the SAOC which render it capable of passing through cell membranes, for example, by designing small, hydrophobic SAOC chemical structures, or by virtue of specific transport systems in the cell which recognize and transport the SAOC into the cell. In addition, the SAOC can be designed for administration only to certain selected cell populations by targeting the SAOC to be recognized by specific cellular uptake mechanisms which bind and take up the SAOC only within select cell populations.

For example, the SAOC may be designed to bind to a receptor found only in a certain cell type, as discussed supra. The SAOC is also designed to recognize and selectively bind to target mRNA sequence, which may correspond to a sequence contained within the sequence shown in SEQ ID NO:2, or SEQ ID NO:4. The SAOC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SAOCs have been shown to be capable of such properties when directed against mRNA targets (see Cohen et al., TIPS, 10:435 (1989) and Weintraub, *Sci. American,* January (1990), pp.40; both incorporated herein by reference).

The present invention also provides compositions containing an acceptable carrier and any of an isolated, purified SCA2 polypeptide, an active fragment thereof, or a purified, mature protein and active fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

Further provided are anti-SCA2 antibodies having specific reactivity with SCA2 polypeptides of the present invention. Active fragments of antibodies are encompassed within the definition of "antibody". Invention antibodies can be produced by methods known in the art using invention polypeptides, proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory (1988)), which is incorporated herein by reference. Invention polypeptides can be used as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338 (1991); Ausubel et al., *Current Protocols in Molecular Biology* (John Wiley and Sons, NY (1989) which are incorporated herein by reference).

Invention antibodies also can be used to isolate invention polypeptides. Additionally the antibodies are useful for detecting the presence of invention polypeptides, as well as analysis of chromosome localization, and structural as well as functional domains. Methods for detecting the presence of SCA2 polypeptides on the surface of a cell comprise contacting the cell with an antibody that specifically binds to SCA2 polypeptides, under conditions permitting binding of the antibody to the polypeptides, detecting the presence of the antibody bound to the cell, and thereby detecting the presence of invention polypeptides on the surface of the cell. With respect to the detection of such polypeptides, the antibodies can be used for in vitro diagnostic or in vivo imaging methods.

Immunological procedures useful for in vitro detection of target SCA2 polypeptides in a sample include immunoassays that employ a detectable antibody. Such immnunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Further, invention antibodies can be used to modulate the activity of the SCA2 polypeptide in living animals, in humans, or in biological tissues or fluids isolated therefrom. Accordingly, compositions comprising a carrier and an amount of an antibody having specificity for SCA2 polypeptides effective to block binding of naturally occurring ligands to invention polypeptides. A monoclonal antibody directed to an epitope of SCA2 polypeptide molecules present on the surface of a cell and having an amino acid sequence substantially the same as an amino acid sequence for a cell surface epitope of an SCA2 polypeptide shown in SEQ ID NO:3, or SEQ ID NO:5, can be useful for this purpose.

The present invention further provides transgenic non-human mammals that are capable of expressing nucleic acids encoding SCA2 polypeptides. Also provided are transgenic non-human mammals capable of expressing nucleic acids encoding SCA2 polypeptides so mutated as to be incapable of normal activity, i.e., do not express native SCA2. The present invention also provides transgenic non-human mammals having a genome comprising antisense nucleic acids complementary to nucleic acids encoding SCA2 polypeptides so placed as to be transcribed into antisense mRNA complementary to mRNA encoding SCA2 polypeptides, which hybridizes thereto and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA having a coding sequence substantially the same as the coding sequence shown in SEQ ID NO:2, or SEQ ID NO:4. An example of a non-human transgenic mammal is a transgenic mouse. Examples of tissue specificity-determining elements are the metallothionein promoter and the L7 promoter.

Animal model systems which elucidate the physiological and behavioral roles of SCA2 polypeptides are produced by creating transgenic animals in which the expression of the SCA2 polypeptide is altered using a variety of techniques. Examples of such techniques include the insertion of normal or mutant versions of nucleic acids encoding an SCA2 polypeptide by microinjection, retroviral infection or other means well known to those skilled in the art, into appropriate fertilized embryos to produce a transgenic animal. (See, for example, Hogan et al., *Manipulating the Mouse Embryo: A Laboratory Manual* (Cold Spring Harbor Laboratory, (1986)).

Another technique, homologous recombination of mutant or normal versions of these genes with the native gene locus in transgenic animals, may be used to alter the regulation of expression or the structure of SCA2 polypeptides (see, Capecchi et al., *Science* 244:1288 (1989); Zimmer et al., *Nature* 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of SCA2 polypeptides.

In contrast to homologous recombination, microinjection adds genes to the host genome, without removing host genes. Microinjection can produce a transgenic animal that is capable of expressing both endogenous and exogenous SCA2 protein. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit protein responses.

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to invention polypeptides. These in vitro screening assays provide information regarding the function and activity of invention polypeptides, which can lead to the identification and design of compounds that are capable of specific interaction with one or more types of polypeptides, peptides or proteins.

In accordance with still another embodiment of the present invention, there is provided a method for identifying compounds which bind to SCA2 polypeptides. The invention proteins may be employed in a competitive binding assay. Such an assay can accommodate the rapid screening of a large number of compounds to determine which compounds, if any, are capable of binding to SCA2 proteins. Subsequently, more detailed assays can be carried out with those compounds found to bind, to further determine whether such compounds act as modulators, agonists or antagonists of invention proteins.

In another embodiment of the invention, there is provided a bioassay for identifying compounds which modulate the activity of invention polypeptides. According to this method, invention polypeptides are contacted with an "unknown" or test substance (in the presence of a reporter gene construct when antagonist activity is tested), the activity of the polypeptide is monitored subsequent to the contact with the "unknown" or test substance, and those substances which cause the reporter gene construct to be expressed are identified as functional ligands for SCA2 polypeptides.

In accordance with another embodiment of the present invention, transformed host cells that recombinantly express invention polypeptides can be contacted with a test compound, and the modulating effect(s) thereof can then be evaluated by comparing the SCA2-mediated response (via reporter gene expression) in the presence and absence of test compound, or by comparing the response of test cells or control cells (i.e., cells that do not express SCA2 polypeptides), to the presence of the compound.

As used herein, a compound or a signal that "modulates the activity" of invention polypeptides refers to a compound or a signal that alters the activity of SCA2 polypeptides so that the activity of the invention polypeptide is different in the presence of the compound or signal than in the absence of the compound or signal. In particular, such compounds or signals include agonists and antagonists. An agonist encompasses a compound or a signal that activates SCA2 protein expression. Alternatively, an antagonist includes a compound or signal that interferes with SCA2 protein expression. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

As understood by those of skill in the art, assay methods for identifying compounds that modulate SCA2 activity generally require comparison to a control. One type of a "control" is a cell or culture that is treated substantially the same as the test cell or test culture exposed to the compound, with the distinction that the "control" cell or culture is not exposed to the compound. For example, in methods that use voltage clamp electrophysiological procedures, the same cell can be tested in the presence or absence of compound, by merely changing the external solution bathing the cell. Another type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

In yet another embodiment of the present invention, the activation of SCA2 polypeptides can be modulated by contacting the polypeptides with an effective amount of at least one compound identified by the above-described bioassays.

In accordance with another embodiment of the present invention, there are provided methods for diagnosing spinocerebellar Ataxia Type 2, said method comprising:
  detecting, in said subject, a genomic or transcribed mRNA sequence having an expanded CAG repeat at a location corresponding to between nucleotides 657 and 724 of SEQ ID NO:2 (FIG. 6). The number of CAG repeats required to indicate spinocerebellar Ataxia Type 2 is substantially above normal, preferably at least about 10–15 CAG repeats above normal, with at least 13 CAG repeats above normal being especially preferred. A normal amount of CAG repeats in the SCA2 gene (SEQ ID NO:2) has been found to be about 22, while 23 CAG repeats is occasionally observed. Thus, in a preferred diagnostic method, at least about 35 CAG repeats are detected between nucleotides 657 and 724 of SEQ ID NO:2 (FIG. 6), with the detection of 37 CAG repeats being especially preferred.

Although expansion of trinucleotide repeats is now recognized as an important mutational mechanism in humans and SCA2 represents the 6th disease in which expansion of a CAG trinucleotide repeat causes disease, there are several features of the SCA2 repeat that appear to be unique. In the other five CAG expansion diseases, the CAG repeats on normal chromosomes are highly polymorphic. Multiple alleles are detected and repeat sizes on normal chromosomes range from a low of 7 repeats in DRPLA to 40 repeats in SCA3/MJD. Heterozygosity for these CAG repeats in the normal population are in the range of 0.80 and above. It has been suggested that the extended normal alleles represent founder alleles which are predisposed to expansion.

The SCA2 repeat is highly unusual, because only two alleles are observed in the normal population. A common allele with 22 repeats is found on 92% of chromosomes, a rare second allele in 8% of chromosomes. Expansion of the SCA2 CAG repeat on disease chromosomes is relatively moderate and is in the range seen with expansions in the SBMA and Huntington's Disease (HD) genes. The lowest number of repeats causing SCA2 was 36 and the most common disease allele had 37 repeats. Disease alleles showing 36 repeats have now clearly been established for HD (Rubinsztein et al., 1996, Am. J. Hum. Genet., 59:16–22), although normal elderly individuals with 36–40 repeats exist and the most common HD alleles have >40 repeats. In contrast to SCA1, where normal and disease alleles may differ by only one repeat unit, the longest normal and the shortest SCA2 disease allele are separated by 13 repeats. Once expanded on disease chromosomes, the SCA2 repeat may undergo moderate expansions.

The SCA2 repeat is contained in a novel gene which is transcribed in several tissues including non-neuronal tissues. The gene product, ataxin-2, has a predicted molecular weight of 140 kDa which is in good agreement with the 150 kDa protein observed using a monoclonal antibody to long polyglutamine tracts. A similar pattern of nearly ubiquitous expression has been observed in the other five polyglutamine diseases. Despite the phenotypic overlap of SCA2 with SCA1 and SCA3, the SCA2 gene shows no homology to these genes.

However, ataxin-2 showed significant homologies with another protein (referred to as "A2RP"; see FIG. 7). A 42 amino acid domain was identified that was 86% identical between the two proteins. The potential functional importance of this domain was underscored by the fact that it was 100% conserved in the mouse SCA2 homologue (FIG. 7). Interestingly, the polyglutamine tract was not conserved in either protein. Since the pathogenesis of polyglutamine containing proteins is still poorly understood, the identification of functionally important domains adjacent to polyglutamine tracts may provide the potential for novel strategies to analyze the function of ataxin-2. A gain of function for the mutated ataxin-2 is supported by the fact that transcripts coding for mutated alleles are detected by RT-PCR.

Expansion of the SCA2 repeat appears to be a common cause of a dominant SCA phenotype in non-Portuguese patients. When samples from 45 families with SCA were screened, samples from 8 independent pedigrees showed expansion of the SCA2 repeat. It has been suggested that there are features specific to SCA2, but this assessment was limited to families large enough to be studied by linkage analysis. A better assessment of the range of SCA2 phenotypes is now possible due to the ability to test small families and single cases. In our patient sample, most patients had a 'typical' SCA phenotype, but some patients had been classified as having an MJD phenotype and others showed a prominent dementia.

When performing direct testing for SCA2 mutations, great caution has to be exercised when interpreting the presence of expanded SCA2 alleles on polyacrylamide gels. A variable number of unrelated PCR fragments may be seen that are in the size range of expanded SCA2 repeats. Although these bands lack the typical 'shadow' bands seen when di- or trinucleotide repeats are amplified, they may interfere with the interpretation in some samples. It is therefore recommended to confirm the presence of an expanded allele by Southern blotting and hybridization with a $(CAG)_{10}$ oligonucleotide.

In yet another embodiment of the present invention, there are provided methods for diagnosing spinocerebellar Ataxia Type 2, said method comprising:

a) contacting nucleic acid obtained from a subject suspected of having SCA2 with primers that amplify at least a nucleic acid fragment of SEQ ID NO:2 containing nucleotides 658–723 of SEQ ID NO:2, under conditions suitable to form a detectable amplification product; and b) detecting an amplification product containing substantially expanded CAG repeats above normal, whereby said detection indicates that said subject has SCA2.

As indicated above, substantially expanded CAG repeats have at least about 10–15 CAG repeats above normal, with at least 13 CAG repeats above normal being especially preferred. Thus, in a preferred diagnostic method, at least about 35 CAG repeats are detected between nucleotides 657 and 724 of SEQ ID NO:2 (FIG. 6), with the detection of 37 CAG repeats being especially preferred.

In accordance with another embodiment of the present invention, there are provided diagnostic systems, preferably in kit form, comprising at least one invention nucleic acid in a suitable packaging material. The diagnostic nucleic acids are derived from SEQ ID NO:2 (FIG. 6), preferably derived from nucleotides 163–657 and nucleotides 724–4098, with primers SCA2-A and SCA2-B being especially preferred. Invention diagnostic systems are useful for assaying for the presence or absence of the extended CAG repeat sequence between nucleotides 657 and 724 of SEQ ID NO:2 in the SCA2 gene in either genomic DNA or in transcribed nucleic acid (such as mRNA or cDNA) encoding SCA2.

A suitable diagnostic system includes at least one invention nucleic acid, preferably two or more invention nucleic acids, as a separately packaged chemical reagent(s) in an amount sufficient for at least one assay. Instructions for use of the packaged reagent are also typically included. Those of skill in the art can readily incorporate invention nucleic probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular extended CAG repeat sequence between the region of genomic DNA corresponding to nucleotides 657 and 724 of SEQ ID NO:2 (FIG. 6), thereby diagnosing the presence of, or a predisposition for, spinocerebellar ataxia type 2. In addition, the packaging material contains instructions indicating how the materials within the kit are employed both to detect a particular sequence and diagnose the presence of, or a predisposition for, spinocerebellar ataxia type 2.

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

All U.S. patents and all publications mentioned herein are incorporated in their entirety by reference thereto. The invention will now be described in greater detail by reference to the following non-limiting examples.

The invention will now be described in greater detail with reference to the following non-limiting examples.

Materials and Methods

Unless otherwise stated, the present invention was performed using standard procedures, as described, for example in Maniatis et al., *Molecular Cloning: A Laboratory Manual*, Cold Spring Harbor Laboratory Press, Cold Spring Harbor, N.Y., USA (1982); Sambrook et al., *Molecular Cloning: A Laboratory Manual* (2 ed.), Cold Spring Harbor Laboratory Press, Cold Spring Harbor, N.Y., USA (1989); Davis et al., *Basic Methods in Molecular Biology*, Elsevier Science Publishing, Inc., New York, USA (1986); or *Methods in Enzymology: Guide to Molecular Cloning Techniques* Vol. 152, S. L. Berger and A. R. Kimmerl Eds., Academic Press Inc., San Diego, USA (1987)).

Libraries. Yeast artificial chromosome (YAC) clones were obtained from the CEPH mega-YAC library and grown under standard conditions (Cohen et al., *Nature* 366:689–701 (1993)). P1 artificial chromosome (PAC) library construction. A 3× human PAC library, designated RPCI-1 (Ioannou et al., Hum. Genet. 219–220 (1994b)) was constructed as described (Ioannou et al., *Nat. Genet.* 6:84–89 (1994a)). The library was arrayed in 384 well dishes. Pools from portion of the library were screened by PCR with AFM154TC5 (D12S1333) and AFMa128yf1 (D12S1332). Subsequently, STSs generated by sequencing of clones using vector primers were used as hybridization probes to gridded colony filters of the PAC library.

YAC DNA preparation. YAC clones were grown in selective media, pelleted and resuspended in 3 ml 0.9 M sorbitol, 0.1 M EDTA pH 7.5, then incubated with 100 U of lytocase (Sigma) at 37° C. for 1 hour. After centrifugation for 5 minutes at 5,000 rpm pellets were resuspended in 3 ml 50 mM Tris pH 7.45, 20 mM EDTA three-tenth ml 10% SDS was added and the mixture was incubated at 65° C. for 30 minutes. One ml of 5 M potassium acetate was added and tubes were left on ice for 1 hour, then centrifuged at 10,000 rpm for 10 minutes. Supernatant was precipitated in 2 volumes of ethanol and pelleted at 6,000 rpm for 15 minutes. Pellets were resuspended in TE, treated with RNase and reextracted with phenol-chloroform.

Analysis by pulsed-field gel electrophoresis. Agarose plugs of yeast cells containing total YAC DNA were prepared (Larin and Lehrach, *Genet. Rcs.* 56:203–208 (1990)) and subjected to pulsed-field gel separation on 1% SeaKem agarose gels in 0.5× TBE using the CHEF DRII Mapper (Bio-Rad). PAC and BAC clones were sized after digestion with XbaI and NotI. Gels were blotted onto Magna NT Nylon membranes using alkaline blotting, UV cross linked and baked at 80° C. for two hours. Membranes were hybridized with total human DNA, washed according to standard procedures, and exposed to Kodak XAR5 film. The sizes of individual clones were determined by comparison to their relative positions with molecular weight standards.

Analysis by fluorescence in situ hybridization (FISH). PAC or BAC clones were biotinylated by nicktranslation in the presence of biotin-14-dATP using the BioNick Labeling Kit (Gibco-BRL). FISH was performed essentially as described (Korenberg et al., *Cytogenet Cell Genet.* 69:196–200 (1995)). Briefly, 400 ng of probe DNA was mixed with 8 ng of human Cot 1 DNA (Gibco-BRL) and 2 ug of sonicated salmon sperm DNA in order to suppress possible background produced from repetitive human sequences as well as yeast sequences in the probe. The probes were denatured at 75° C., preannealed at 37° C. for one hour, and applied to denatured chromosome slides prepared from normal male lymphocytes (Korenberg et al., 1995, supra). Post-hybridization washes were performed at 40° C. in 2× SSC/50% formamide followed by washes in 1× SSC at 50° C. Hybridized DNAs were detected with avidin-conjugated fluorescent isothiocyanate (Vector Laboratories). One amplification was performed by using biotinylated anti-avidin. For distinguishing chromosome subbands precisely, a reverse banding technique was used, which was achieved by chromomycin A3 and distamycin A double staining (Korenberg et al., 1995, supra). The color images were captured by using a Photometrics Cooled-CCD camera and BDS image analysis software (Oncor Imaging, Inc.).

PAC and BAC DNA preparation. Selected clones were grown overnight in LB media containing 12.5 $\mu$g/ml kanamycin for PACs and 12.5 $\mu$g/ml chloramphenicol for BACs. DNAs were prepared by the alkaline lysis method. PAC DNAs were digested with NotI and subjected to pulsed-field gel electrophoresis. Sizes were determined relative to $\lambda$ concatamers.

Southern blot analysis. Gel electrophoresis of DNA was carried out on 0.8% agarose gels in 1× TBE. Transfer of nucleic acids to Nybond N+ nylon membrane (Amersham) was performed according to the manufacturer's instruction. Probes were labelled using RadPrime Labeling System (BRL). Hybridization was carried out at 42° C. for 16 hours in 50% formamide, 5× SSPE, 5× Denhardt's 0.1% SDS, 100 mg/ml denatured salmon sperm DNA. The filters were washed once in 1× SSC, 0.1% SDS at room temperature for 20 minutes, and twice in 0.1× SSC, 0.1% SDS for 20 minutes at 65° C. The blots were exposed onto X-ray film (Kodak, X-OMAT-AR).

Sequencing of PAC endclones. PAC clones were inoculated into 500 ml of LB/kanamycin and grown overnight. DNAs were isolated using QIAGEN columns according to the vendors protocol with one additional phenol/chloroform/isoamylalcohol extraction followed by one additional chloroform/isoamylalcohol extraction. Clones were sequenced using the Gibco-BRL cycle sequencing kit with standard T7 and SP6 primers.

Hybridization of $(CAG)_{10}$ oligonucleotides. Eighty ng of oligonucleotide were -5' end-labeled and hybridized overnight at 42° C. in buffer containing 1 M NaCl, 0.05 M Tris HCl pH7, 5.5 mM EDTA, 0.1% SDS, 1× Denhardt's solution and 200 $\mu$g/ml denatured salmon sperm DNA. Filters were washed 2 times with 2× SSC, 0.1% SDS at 55° C. and exposed to Kodak X-ray film for 24 hours, and subsequently washed at 65° C., followed by additional exposure to X-ray film.

Regression Analysis. The data were fit using the Statistical Analysis Software (SAS) package version 3.10 using the Secant Method (Ralston et al, 1978, *Technometrics*, 20:7–14). The regression equation was y=A*exp(-ax), where y gives the age of onset and x the number of CAG repeats. The conversion criteria were met with the mean square error of 76.598. The value of parameters are as follows: A=1171.583, a=0.091.

EXAMPLE 1

Physical Map of the SCA2 region

BAC library construction of total human genomic DNA was performed as described in Shizuya et al., *Proc. Natl. Acad. Sci. USA* 89:8794–8797 (1992). BAC clones were screened by PCR using STSs (D12S1228, S29, S32, S33). Insert size of clones was measured by running pulsed-field gel electrophoresis after digesting DNA with NotI.

The marker AFMa128yf1(D12S1332) which was non-recombinant in several SCA2 pedigrees served as the starting point to assemble a PAC contig. This was done by screening PCR pools of a 3× human PAC library (Ioannou et al., 1994). Two clones were positive for this STS (FIG. 1). Single copy sequences from PAC ends were obtained from P168L1 and used to extend this contig. Subsequent 'walking steps, however, were undertaken by hybridizing PCR-generated STS fragments to gridded membranes of the 3× PAC library and the 1× total human genome BAC library (Research Genetics).

In a similar fashion, a second contig was established starting with the telomeric flanking marker AFM154tc5 (D12S1333). A total of two clones were identified by screening of PCR pools. After several walking steps, overlap of the two contigs was established by shared STSs (FIG. 1) and by shared restriction fragments (data not shown). All STSs shown in FIG. 1 were mapped back to human chromosome 12 by PCR analysis of a human/Chinese hamster somatic hybrid cell line, HHW582, which contains CHR 12 as the only human chromosome, and by analysis of a chromosome 12 specific lambda library, LL12NS01 (both from Coriell Cell Repositories). Map position in 21q24.1 for clones B295CO5, P191C5 and P65I22 was confirmed using FISH (FIG. 1b).

At the same time contigs were constructed for the other flanking markers AFM240wel (D12S1328), AFM291xxe9 (D12S329), and markers WI-4176 and WI-6850 (data not shown). These contigs did not overlap with one another, nor with the AFMa128yf1/AFM154tc5 contig.

All PAC and BAC clones were sized by pulsed-field electrophoresis after digestion with NotI. Overlap of clones was initially determined by shared STS content, and subsequently confirmed by hybridization of selected clones to Southern blots of NotI/XbaI digests of clones.

The dense localization of STSs allowed the precise positioning of YACs that had been identified by screening of PCR pools of the CEPH mega-YAC library with either AFMa128yf1 or AFM154tc5. The only YAC that was positive for both AFMa128yf1 (D12S1332) and AFM154tc5, Y884_h_11, contained an approximately 200 kb interstitial deletion. A small portion of this deletion was not covered by any of the other YAC clones.

EXAMPLE 2

Identification of SCA2-related trinucleotide repeats

Since we had observed marked anticipation in one pedigree with SCA2, we identified clones containing trinucleotide repeats. EcoRI digests of a minimal tiling path of PAC clones were hybridized with a $(CAG)_{10}$ nucleotide, as well as other trinucleotide permutations. Three CAG positive bands of distinct sizes were identified in the contig.

PAC clone P65I22 was digested with Sau3A and subcloned into the pBluescript SK (+) phagemid (Stratagene). After transfection into DH5α, bacterial colonies were screened for poly-CAG containing inserts using the methods described above. Positive clones were sequenced using the Circum Vent cycle sequencing kit (New England Biolabs) with end-labeled T3 and T7 primers. However, no reliable sequence could be obtained from the initial plasmid PL65I22. Therefore, this plasmid was digested with BssHII, recloned into the pBluescript plasmid, and CAG-positive clones sequenced with primers corresponding to the following nucleotides of the vector sequence (primer A: 828–848, primer B: 547–565). The sequence of this plasmid, designated PL65I22B, allowed the generation of primers SCA2-A and SCA2-B, which were used to confirm the sequence flanking the CAG repeat.

Plasmid PL65I22B containing an extended CAG repeat that appeared to be embedded into a long open reading frame (ORF) (FIG. 2; SEQ ID NO:1). Sequence analysis of this plasmid appeared to be extremely difficult due to the abundant presence of premature terminations (see below). The CAG repeat in PL65I22B was twice interrupted and had the following structure $(CAG)_8CAA(CAG)_4CAA(CAG)_8$. Four additional PAC clones and one BAC clone contained the SCA2 repeat, and all clones had 22 repeats with two CAA interruptions. Analysis of the genomic DNA sequence flanking the CAG repeat suggested the presence of an open reading frame (see also FIG. 6) and a potential splice site 3' of the CAG repeat (vertical arrow in FIG. 2).

The difficulties encountered in sequencing this region suggested that stable secondary structures might be formed in this GC-rich region. Previous analysis of trinucleotide repeats predisposed to expansion had suggested that these regions are predicted to form hairpin structures. We used an up-dated version of the DNA-FOLD Program (SantaLucia et al., 1996, *Biochemistry* 35:3555–3562) for secondary structure predictions.

Subsequent analysis of the sequence flanking the CAG repeat using the OLIGO Program indicated that it contained several palindromic sequences predicted to form hairpin loops. Despite the predicted hairpin structures sufficient sequence information was generated to design primers flanking the CAG repeat for the PCR analysis of patient samples.

EXAMPLE 3

Genomic analysis of an extended CAG SCA2 repeat

Using primer pairs SCA2-A and B, genomic DNAs from normal controls and SCA2 patients were amplified and separated by agarose gel electrophoresis. The best results were obtained at an annealing temperature of 63° C. with denaturation times of 90 sec.

Eighty ng each of primers SCA2-A (5'-GGG CCC CTC ACC ATG TCG-3')(SEQ ID NO:6) and SCA2-B (5'-CGG GCT TGC GGA CAT TGG-3')(SEQ ID NO:7) were added to 20 ng of human DNA with standard PCR buffer and nucleotide concentrations. After an initial denaturation at 95° C. for 5 minutes, 35 cycles were repeated with denaturation at 96° C. for 1.5 minutes, an annealing temperature of 63° C. for 30 seconds, extension at 72° C. for 1.5 minutes, and a final extension of 5 minutes at 72° C.

PCR products obtained by PCR amplification of genomic DNAs were separated by electrophoresis through 2% agarose gels in 1× TBE buffer at 10 V/cm. Gels were transferred to nylon membranes (MSI, Westborough, Mass.) using standard procedures for Southern blotting. Membranes were hybridized with a $(CAG)_{10}$ oligonucleotide and processed as described above.

On agarose electrophoresis, a single band of approximately 130 bp was detected in 20 normal individuals, although occasionally two closely spaced bands could be observed. In contrast, all 15 patients with SCA2 from 3 independent famalies showed one allele in the normal size range and a larger allele ranging from approximately 190 to 250 bp. Southern blot analysis confirmed that both alleles contained CAG repeats.

Figure 3:
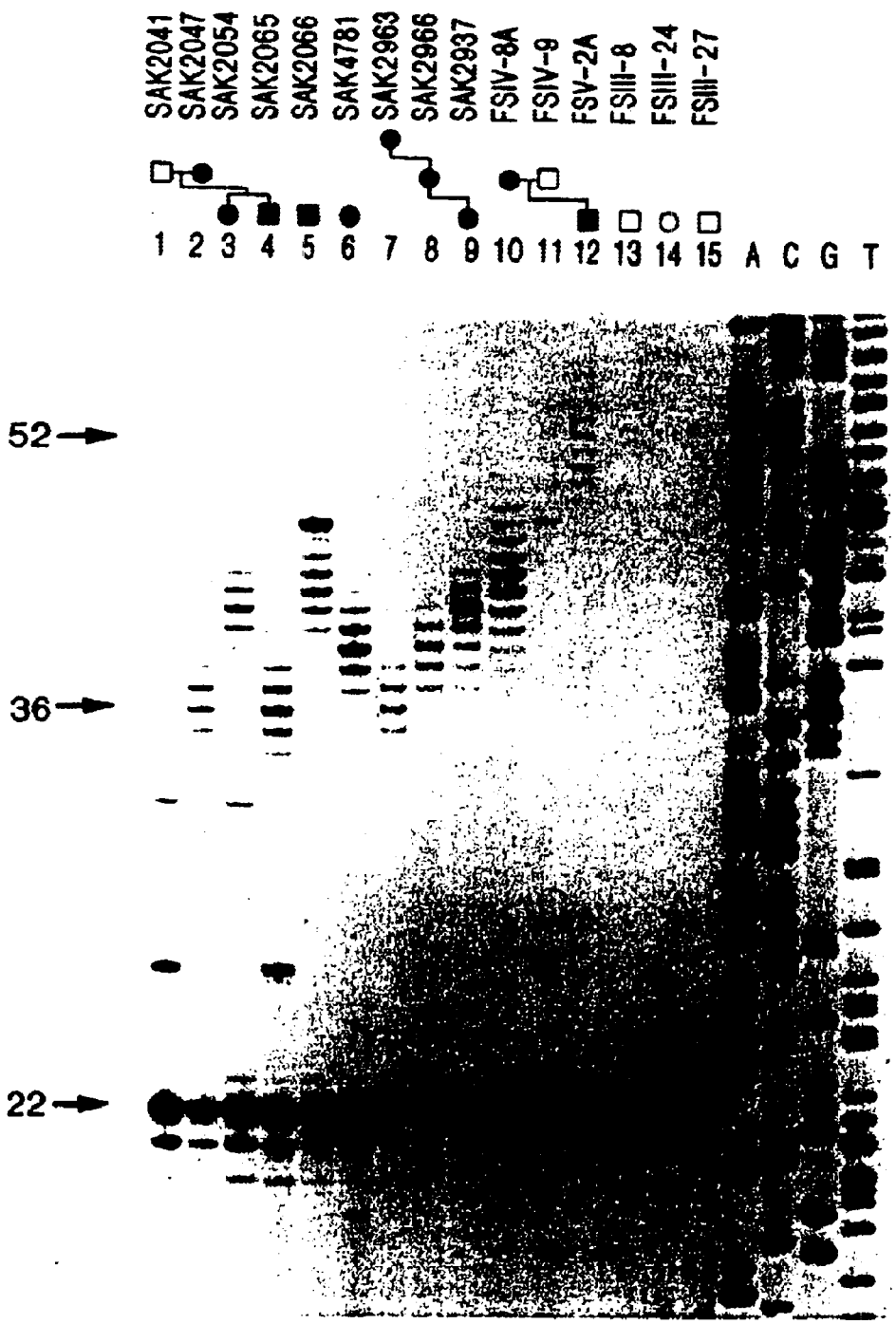
FIG. 3 shows an analysis of the SCA2 CAG repeat by polyacrylamide electrophoresis. A common allele of 22 repeats and a less frequent allele of 23 repeats (samples 14 and 15) are seen in normal individuals. SCA2 patients with extended alleles form 37 to 52 repeats are shown. SCA2 patients derive from two pedigrees with CHR 12 linked dominant ataxia. The pedigree structures are shown at the top. Genomic DNAs were amplified with primers SCA2-A and SCA2-B and separated in a 6% polyacrylamide gel. Primer SCA2-A was end-labeled. As a size standard, single stranded M13mp18 control DNA was sequenced with sequencing primer "–40" provided by USB (United States Biochem.).
Figure 4:
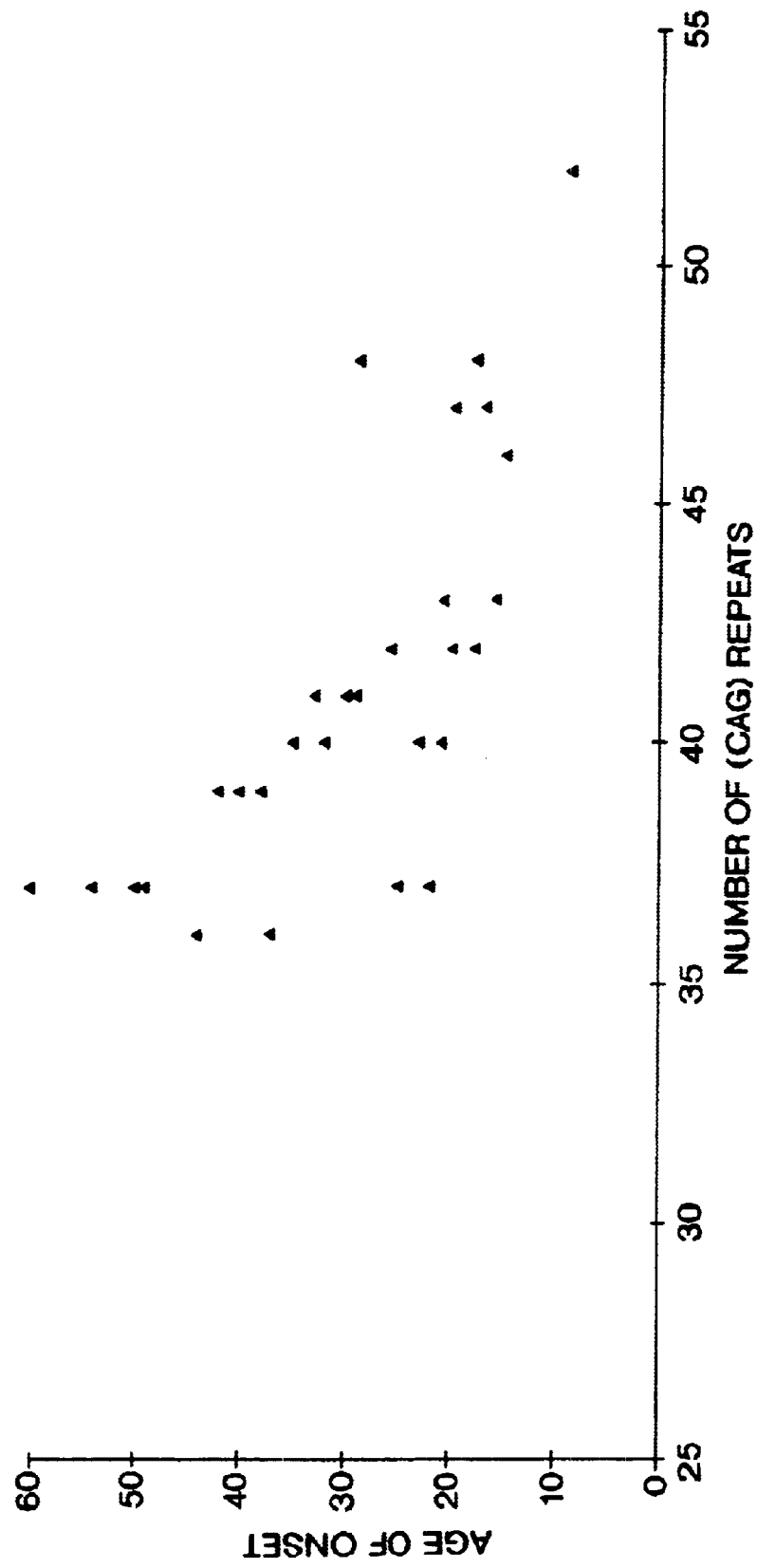
FIG. 4 shows a Scattergram indicating that CAG repeat length and age-of-onset of disease in 33 SCA2 patients are inversely correlated.

To determine the exact sizes of amplified fragments, DNAs from SCA2 patients and 50 normal individuals were amplified and PCR products separated by polyacrylamide gel electrophoresis. A common allele of 22 repeats and a less frequent allele of 23 repeats were observed on normal chromosomes (FIG. 3). The allele frequencies were 0.92 for the smaller and 0.08 for the larger allele. In patients from three independent SCA2 pedigrees, however, extended alleles ranging from 36 to 52 repeats were observed (FIG. 3). Once expanded to the pathologic range, the SCA2 repeat was moderately unstable and further expansion by 2 to 9 repeat units was observed during meiosis (FIG. 3). There was great variability of the age of onset for a given repeat length, especially for disease alleles with 36–40 repeats (FIG. 4). Due to the heterogeneous variance of age of onset we used non-linear regression, and an exponential function was successfully fitted (see methods and FIG. 4). The smallest expansion of 36 repeats was seen in two men with disease onset at ages 37 and 44. The longest expansion of 52 repeats was seen in a boy with disease onset at 9 years of age.

Sequence analysis of ten normal alleles revealed that the common normal allele with 22 repeats contained the two CAA interruptions that were also detected in plasmid PL65I22B. The less frequent normal allele with 23 repeats had lost the 5' CAA interruption, and contained an additional CAG repeat at the 5'-end of the repeat. In three expanded alleles that were isolated from SCA2 patients the CAG repeat lacked any interruptions.

To determine the frequency of mutation in the SCA2 gene in non-Portuguese patients we screened DNAs from 45 independent families with autosomal dominant SCAs. Expansion of the SCA2 repeat was detected in six families. In this set of families, SCA2 expansion was twice as common as expansion in the SCA1 gene. In addition to individuals with a 'typical' SCA phenotype, expansion of the SCA2 repeat was detected in a pedigree with a MJD phenotype and one family with SCA and marked dementia.

EXAMPLE 4

Isolation of human SCA2 cDNA cDNA library screen: $^{32}$P-labeled probes were generated by PCR amplification of plasmid P65I22B using the following primer pair: 65A3: 5'CCGCGGCTGCCAATGTCC, (SEQ ID NO:8) 65B5: 5'GTAACCGTTCGGCGCCCG (SEQ ID NO:9). A second probe was generated using primers 65A6: 5'GGCTCCCGGCGGCTCCTT (SEQ ID NO:10), 65B6: 5'TGCTGCTGCTGCTGGGGCTTCAG. Screening of the trisomy 21 fetal brain cDNA library and the Stratagene adult human frontal cortex cDNA Lamba Zap II library was performed using the amplification products generated from plasmid P65I22B. Phages were plated to an average density of 1× $10^5$ per 150 $cm^2$ plate. Plaque lifts of 20 plates (2×$10^6$ phages) were made using duplicated nylon membranes (Duralose-UV, Stratagene). Hybridization and excision were performed according to the manufacturer's protocol. Hybridized membranes were washed to a final stringency of 0.2× SSC, 0.1× SDS at 65° C. The filters were exposed overnight onto X-ray film. Excised phagemids were grown overnight in 5 ml LB medium containing 50 ug/ml of ampicillin.

Figure 5:
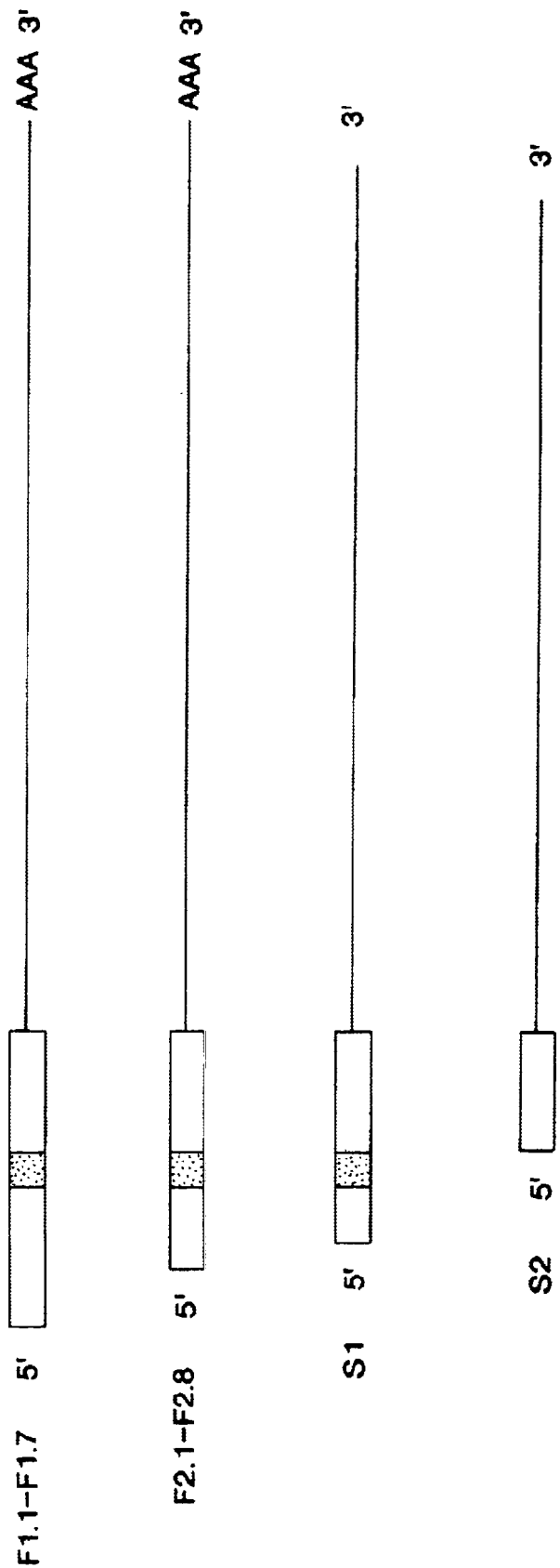
FIG. 5 shows four cDNA clones as a schematic of the composite SCA2 cDNA sequence. The thick line corresponds to coding sequence, the thin line to untranslated regions. The location of the CAG repeat is indicated by a hatched box. In clone S2, the repeat was not a CAG, but a CTG repeat followed by 12 bp of sequence not contained in any of the other cDNA clones.

Using PCR-generated fragments containing nucleotides 39–237 and 262 to 397 (according to the sequence shown in FIG. 2) we initially screened a human adult frontal cortex library (Stratagene). Through screening of 0.8×$10^6$ clones, two positive clones, S1 and S2, were identified. To obtain additional clones, 2×$10^6$ clones of a human fetal brain library generated from a fetus with trisomy 21 (Yamakawa et al., 1995, Hum. Mol. Genet., 4:709–716) were screened using the same PCR-generated fragments. A total of 15 clones were obtained, all of which were partially sequenced to determine alignment of clones. These clones appeared to belong to a total of two classes of clones (designated F1.1 through F1.7 and F2.1 through F2.8) that contained long portions of the 3' untranslated region and a poly-A tail (FIG. 5). Both classes of clones extended 40 and 265 bp 5' of the CAG repeat in the coding region of the SCA2 gene.

To obtain cDNA sequence for the 5' end of the SCA2 coding region, placental poly-T selected placental mRNAs (Clontech) were transcribed with MMLV reverse transcriptase and amplified with the following primer pairs: SCA2-A30: 5° CCGCCCGCTCCTCACGTGT(SEQ ID NO:12), SCA2-A31: 5'ACCCCCGAGAAAGCAACC(SEQ ID NO:13); SCA2-B30: 5'-CCGTTGCCGTTGCTACCA (SEQ ID NO:14). The sequences for primers SCA2-A30 and A31 were obtained from genomic sequence, and are located 5' to the stop codon preceding the putative initiator methionine. The sequence for SCA2-B30 was obtained from the 5' end of cDNA clones F1.1 and F1.2. The amplicons obtained by RT-PCR were directly sequenced.

The composite of the human SCA2 cDNA sequence assembled from several overlapping cDNA clones is shown in FIG. 6 (SEQ ID NO:2). The longest open reading frame consists of 3936 bp and ends with a TAA termination codon. The stop codon is followed by 364 bp of 3' untranslated sequence. The CAG repeat is located in the 5'end of the coding region. The putative translation start site follows an in frame stop codon located 78 bp upstream. The predicted molecular weight for the SCA2 translation product is 140.1 kDa with the CAG trinucleotide repeat predicted to code for glutamine. In analogy to the SCA1 gene product, we propose the name ataxin-2 for the SCA2 gene product.

The cDNA sequence was compared against the GenBank database using the FASTA sequence alignment algorithms and the TIGR database. The predicted protein sequence was compared against the SwissProt database and the predicted translation products of the GenBank database. These searches revealed no significant similarities to genes of known function except for limited homologies to the GLI-Krueppel related protein YY1 (nucleotides 45 to 586, odds against chance occurrence 6.6×$10^{-7}$).

However, significant similarities were detected with two partial cDNA transcripts in the TIGR database (THC148678, H03566, odds against chance similarity <$10^{31}$). Complete sequence analysis of these cDNA clones (purchased from ATCC) revealed significant homologies with ataxin-2. This protein was named ataxin-2 related protein (A2RP). The region showing the most significant homology including a domain of 42 amino acids with 86% identity (codons 243–284 of the consensus sequence) is shown in FIG. 7. This domain is also 100% conserved in mouse ataxin-2. Despite the significant homologies, the polyglutamine tract in ataxin-2 was replaced with an interrupted polyproline tract in the related A2RP human protein and was reduced to one glutamine in the mouse SCA2 homologue (see FIG. 7).

EXAMPLE 6

RT-PCR and Northern blot analysis:

RNA isolation and reverse transcription was carried out using well-known methods (Huynh et al., 1994, Hum. Mol. Genet, 3:1075–1079). RNAs were isolated from lymphoblastoid cell lines established from patients and unrelated spouses in the FS pedigree with SCA2 (Pulst et al., 1993, Nat. Genet., 5:8–10). Multiple tissue Northern blots were purchased from Clontech. For amplification, primers located in two exons (SCA-A and SCA-B14, see also FIG. 6) were chosen so that genomic DNA was not amplified. The sequence for SCA-B14 was: 5'TTCTCATGTGCGGCATC AAG(SEQ ID NO:15)

Using RT-PCR, it was determined that the SCA2 CAG repeat was transcribed in lymphoblastoid cell lines. In cDNAs from SCA2 patients, transcription from both the normal and the expanded allele was detected using oligonucleotide primers that flank the repeat. By Northern blot analysis, the SCA2 gene was determined to be widely expressed. A strong signal corresponding to a 4.5 kb transcript was detected in all brain regions examined. This transcript was also detected-in RNAs isolated from heart, placenta, liver, skeletal muscle, and pancreas. Little transcript was detected in lung and no transcription was detectable in kidney. A much fainter transcript of 7.5 kb could be seen in RNAs isolated from some brain regions and in some peripheral tissues.

EXAMPLE 7

Isolation of mouse SCA2 cDNA

To identify mouse SCA2 cDNA clones, the Stratagene Lambda ZAP newborn mouse brain cDNA library was screened with a human SCA2 cDNA clone. Six clones were identified and sequenced. A partial mouse SCA2 cDNA is set forth in SEQ ID NO:4.

SUMMARY OF SEQUENCES

SEQ ID NO:1 is the genomic nucleic acid sequence set forth in FIG. 2.

SEQ ID NO:2 is the nucleic acid sequence (and the deduced amino acid sequence) of a cDNA encoding a human-derived SCA2 protein of the present invention (also set forth in FIG. 6).

SEQ ID NO:3 is the deduced amino acid sequence of the human-derived SCA2 protein set forth in SEQ ID NO:2.

SEQ ID NO:4 is the nucleic acid sequence (and the deduced amino acid sequence) of a cDNA encoding a mouse-derived SCA2 protein of the present invention.

SEQ ID NO:5 is the deduced amino acid sequence of the mouse-derived SCA2 protein set forth in SEQ ID NO:4.

What is claimed is:

1. A method for determining whether a human is negative for spinocerebellar ataxia type 2 in a human nucleic acid sample comprising the steps of:

amplifying said nucleic acid sample with a first primer and a second primer by polymerase chain reaction wherein said first primer hybridizes to a region of nucleotides 193 to 264 of SEQ ID NO: 1 and said second primer hybridizes to a region of nucleotides 333 to 509 of SEQ ID NO:1 obtaining an amplification product of said nucleic acid sample by said polymerase chain reaction; and measuring a number of CAG repeals in said amplification product, wherein 22 CAG repeats in said nucleic acid sample would be negative for spinocerebellar Ataxia type 2.

2. A method for detecting the presence of a nucleic acid molecule comprising obtaining a human nucleic acid sample and detecting the presence of the nucleic acid molecule represented by SEQ ID NO:1 in a human nucleic acid sample.

3. A method for detecting the presence of CAG repeated comprising obtaining a human nucleic acid sample and detecting the presence of a CAG repeated in the nucleic acid molecule represented by SEQ ID NO:1 in a human nucleic acid sample.

4. A method for detecting the presence of a CAG repeat comprising obtaining a human nucleic acid sample and detecting the presence of a 45 CAG repeat in the nucleic acid molecule represented by SEQ ID NO:1 in a human nucleic acid sample.

* * * * *

UNITED STATES PATENT AND TRADEMARK OFFICE
CERTIFICATE OF CORRECTION

PATENT NO. : 6,673,535 B1
APPLICATION NO. : 09/083268
DATED : January 6, 2004
INVENTOR(S) : Stefan M. Pulst It is certified that error appears in the above-identified patent and that said Letters Patent is hereby corrected as shown below:

On page 1 before the Background of the Invention section, insert the following:

--GOVERNMENT SUPPORT
 The invention was supported, in whole or in part, by a grant NIH RO1 NS33123-01 A2 from the National Institutes of Health (NIH). The Government has certain rights in the invention.--.

Column 4

Line 36, delete "FIG." and insert --FIG. 6A--;
Line 40, delete "FIG 6)." and insert --FIG. 6A).--;
Line 64, delete "FIG. 6" and insert --FIG. 6A-C--.

Column 5

Line 12, delete "FIG. 6" and insert --FIG. 6A--.

Column 6

Line 21, delete "(FIG. 6)," and insert --(FIG. 6A-C),--;
Line 67, delete "(FIG. 6)," and insert --(FIG. 6A-C),--.

Column 7

Line 18, delete "(FIG. 6)" and insert --(FIG. 6A-C)--.

Column 8

Line 20, delete "(FIG. 6)," and insert --(FIG. 6A-C),--;
Line 26, delete "(FIG. 6)," and insert --(FIG. 6A-C),--.

Column 10

Line 44, delete "(FIG. 6)," and insert --(FIG. 6A-C),--.

Column 15

Line 59, delete "(FIG. 6)." and insert --(FIG. 6A).--.

UNITED STATES PATENT AND TRADEMARK OFFICE
CERTIFICATE OF CORRECTION

| | |
|---|---|
| PATENT NO. | : 6,673,535 B1 |
| APPLICATION NO. | : 09/083268 |
| DATED | : January 6, 2004 |
| INVENTOR(S) | : Stefan M. Pulst |

It is certified that error appears in the above-identified patent and that said Letters Patent is hereby corrected as shown below:

<u>Column 16</u>

Line 3, delete "(FIG. 6)," and insert --(FIG. 6A),--.

<u>Column 17</u>

Line 35, delete "(FIG. 6)," and insert --(FIG. 6A),--;
Line 41, delete "(FIG. 6)," and insert --(FIG. 6A-C),--;
Line 67, delete "(FIG. 6)," and insert --(FIG. 6A),--.

<u>Column 21</u>
Line 40, delete "(FIG. 6)" and insert --(FIG. 6A)--.

<u>Column 23</u>

Line 50, delete "FIG. 6" and insert --FIG. 6A-C--.

<u>Column 24</u>

Line 56, delete "FIG. 6)." and insert --FIG. 6A-C).--.

<u>Column 55</u>

Line 67, delete "reaction" and insert --reaction,--.

<u>Column 56</u>

Line 65, after SEQ ID NO: 1, add --;--.

UNITED STATES PATENT AND TRADEMARK OFFICE
CERTIFICATE OF CORRECTION

PATENT NO. : 6,673,535 B1
APPLICATION NO. : 09/083268
DATED : January 6, 2004
INVENTOR(S) : Stefan M. Pulst It is certified that error appears in the above-identified patent and that said Letters Patent is hereby corrected as shown below:

Column 57

Line 1, delete "repeals" and insert --repeats--;
Line 4, delete "Ataxia" and insert --ataxia--;
Line 10, delete "of CAG repeated" and insert --of a CAG repeat--.

Signed and Sealed this

Thirteenth Day of November, 2007

JON W. DUDAS
*Director of the United States Patent and Trademark Office*

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 516 base pairs
      (B) TYPE: nucleic acid
      (C) STRANDEDNESS: both
      (D) TOPOLOGY: both (ii) MOLECULE TYPE: DNA (genomic)

(xi) SEQUENCE DESCRIPTION: SEQ ID NO:1:

```
TTGGTAGCAA CGGAAACGGC GGCGGCGCGT TTCGGCCCGG CTCCCGGCGG CTCCTTGGTC    60

TCGGCGGGCC TCCCCGCCCC TTCGTCGTCG TCCTTCTCCC CCTCGCCAGC CCGGGCGCCC   120

CTCCGGCCGC GCCAACCCGC GCCTCCCCGC TCGGCGCCCG TGCGTCCCCG CCGCGTTCCG   180

GCGTCTCCTT GGCGCGCCCG GCTCCCGGCT GTCCCCGCCC GGCGTGCGAG CCGGTGTATG   240

GGCCCCTCAC CATGTCGCTG AAGCCCCAGC AGCAGCAGCA GCAGCAGCAG CAACAGCAGC   300

AGCAGCAACA GCAGCAGCAG CAGCAGCAGC AGCCGCCGCC CGCGGCTGCC AATGTCCGCA   360

AGCCCGGCGG CAGCGGCCTT CTAGCGTCGC CCGCCGCCGC GCCTTCGCCG TCCTCGTCCT   420

CGGTCTCCTC GTCCTCGGCC ACGGCTCCCT CCTCGGTGGT CGCGGCGACC TCCGGCGGCG   480

GGAGGCCCGG CCTGGGCAGG TGGGTGTCGG CACCCC                             516
```

(2) INFORMATION FOR SEQ ID NO:2:

(i) SEQUENCE CHARACTERISTICS:
      (A) LENGTH: 4481 base pairs
      (B) TYPE: nucleic acid
      (C) STRANDEDNESS: both
      (D) TOPOLOGY: both (ii) MOLECULE TYPE: cDNA (ix) FEATURE:
      (A) NAME/KEY: CDS
      (B) LOCATION: 163..4101

(xi) SEQUENCE DESCRIPTION: SEQ ID NO:2:

```
ACCCCCGAGA AAGCAACCCA GCGCGCCGCC CGCTCCTCAC GTGTCCCTCC CGGCCCCGGG    60

GCCACCTCAC GTTCTGCTTC CGTCTGACCC CTCCGACTTC CGGTAAAGAG TCCCTATCCG   120

CACCTCCGCT CCCACCCGGC GCCTCGGCGC GCCCGCCCTC CG ATG CGC TCA GCG      174
                                                 Met Arg Ser Ala
                                                  1

GCC GCA GCT CCT CGG AGT CCC GCG GTG GCC ACC GAG TCT CGC CGC TTC    222
Ala Ala Ala Pro Arg Ser Pro Ala Val Ala Thr Glu Ser Arg Arg Phe
  5                  10                  15                  20

GCC GCA GCC AGG TGG CCC GGG TGG CGC TCG CTC CAG CGG CCG GCG CGG    270
Ala Ala Ala Arg Trp Pro Gly Trp Arg Ser Leu Gln Arg Pro Ala Arg
                 25                  30                  35

CGG AGC GGG CGG GGC GGC GGT GGC GCG GCC CCG GGA CCG TAT CCC TCC    318
Arg Ser Gly Arg Gly Gly Gly Gly Ala Ala Pro Gly Pro Tyr Pro Ser
             40                  45                  50

GCC GCC CCT CCC CCG CCC GGC CCC GGC CCC CCT CCC TCC CGG CAG AGC    366
Ala Ala Pro Pro Pro Pro Gly Pro Gly Pro Pro Pro Ser Arg Gln Ser
         55                  60                  65
```

```
TCG CCT CCC TCC GCC TCA GAC TGT TTT GGT AGC AAC GGC AAC GGC GGC          414
Ser Pro Pro Ser Ala Ser Asp Cys Phe Gly Ser Asn Gly Asn Gly Gly
    70                  75                  80

GGC GCG TTT CGG CCC GGC TCC CGG CGG CTC CTT GGT CTC GGC GGG CCT          462
Gly Ala Phe Arg Pro Gly Ser Arg Arg Leu Leu Gly Leu Gly Gly Pro
85                  90                  95                  100

CCC CGC CCC TTC GTC GTC GTC CTT CTC CCC CTC GCC AGC CCG GGC GCC          510
Pro Arg Pro Phe Val Val Val Leu Leu Pro Leu Ala Ser Pro Gly Ala
                105                 110                 115

CCT CCG GCC GCG CCA ACC CGC GCC TCC CCG CTC GGC GCC CGT GCG TCC          558
Pro Pro Ala Ala Pro Thr Arg Ala Ser Pro Leu Gly Ala Arg Ala Ser
        120                 125                 130

CCG CCG CGT TCC GGC GTC TCC TTG GCG CGC CCG GCT CCC GGC TGT CCC          606
Pro Pro Arg Ser Gly Val Ser Leu Ala Arg Pro Ala Pro Gly Cys Pro
            135                 140                 145

CGC CCG GCG TGC GAG CCG GTG TAT GGG CCC CTC ACC ATG TCG CTG AAG          654
Arg Pro Ala Cys Glu Pro Val Tyr Gly Pro Leu Thr Met Ser Leu Lys
150                 155                 160

CCC CAG CAG CAG CAG CAG CAG CAG CAA CAG CAG CAG CAG CAA CAG              702
Pro Gln Gln Gln Gln Gln Gln Gln Gln Gln Gln Gln Gln Gln Gln
165                 170                 175                 180

CAG CAG CAG CAG CAG CAG CAG CCG CCG CCC GCG GCT GCC AAT GTC CGC          750
Gln Gln Gln Gln Gln Gln Gln Pro Pro Pro Ala Ala Ala Asn Val Arg
                185                 190                 195

AAG CCC GGC GGC AGC GGC CTT CTA GCG TCG CCC GCC GCC GCG CCT TCG          798
Lys Pro Gly Gly Ser Gly Leu Leu Ala Ser Pro Ala Ala Ala Pro Ser
        200                 205                 210

CCG TCC TCG TCC TCG GTC TCC TCG TCC TCG GCC ACG GCT CCC TCC TCG          846
Pro Ser Ser Ser Ser Val Ser Ser Ser Ser Ala Thr Ala Pro Ser Ser
            215                 220                 225

GTG GTC GCG GCG ACC TCC GGC GGC GGG AGG CCC GGC CTG GGC AGA GGT          894
Val Val Ala Ala Thr Ser Gly Gly Gly Arg Pro Gly Leu Gly Arg Gly
230                 235                 240

CGA AAC AGT AAC AAA GGA CTG CCT CAG TCT ACG ATT TCT TTT GAT GGA          942
Arg Asn Ser Asn Lys Gly Leu Pro Gln Ser Thr Ile Ser Phe Asp Gly
245                 250                 255                 260

ATC TAT GCA AAT ATG AGG ATG GTT CAT ATA CTT ACA TCA GTT GTT GGC          990
Ile Tyr Ala Asn Met Arg Met Val His Ile Leu Thr Ser Val Val Gly
                265                 270                 275

TCC AAA TGT GAA GTA CAA GTG AAA AAT GGA GGT ATA TAT GAA GGA GTT         1038
Ser Lys Cys Glu Val Gln Val Lys Asn Gly Gly Ile Tyr Glu Gly Val
        280                 285                 290

TTT AAA ACT TAC AGT CCG AAG TGT GAT TTG GTA CTT GAT GCC GCA CAT         1086
Phe Lys Thr Tyr Ser Pro Lys Cys Asp Leu Val Leu Asp Ala Ala His
            295                 300                 305

GAG AAA AGT ACA GAA TCC AGT TCG GGG CCG AAA CGT GAA GAA ATA ATG         1134
Glu Lys Ser Thr Glu Ser Ser Ser Gly Pro Lys Arg Glu Glu Ile Met
310                 315                 320

GAG AGT ATT TTG TTC AAA TGT TCA GAC TTT GTT GTG GTA CAG TTT AAA         1182
Glu Ser Ile Leu Phe Lys Cys Ser Asp Phe Val Val Val Gln Phe Lys
325                 330                 335                 340

GAT ATG GAC TCC AGT TAT GCA AAA AGA GAT GCT TTT ACT GAC TCT GCT         1230
Asp Met Asp Ser Ser Tyr Ala Lys Arg Asp Ala Phe Thr Asp Ser Ala
                345                 350                 355

ATC AGT GCT AAA GTG AAT GGC GAA CAC AAA GAG AAG GAC CTG GAG CCC         1278
Ile Ser Ala Lys Val Asn Gly Glu His Lys Glu Lys Asp Leu Glu Pro
        360                 365                 370

TGG GAT GCA GGT GAA CTC ACA GCC AAT GAG GAA CTT GAG GCT TTG GAA         1326
Trp Asp Ala Gly Glu Leu Thr Ala Asn Glu Glu Leu Glu Ala Leu Glu
            375                 380                 385
```

| | | |
|---|---|---|
| AAT GAC GTA TCT AAT GGA TGG GAT CCC AAT GAT ATG TTT CGA TAT AAT<br>Asn Asp Val Ser Asn Gly Trp Asp Pro Asn Asp Met Phe Arg Tyr Asn<br>390 395 400 | | 1374 |
| GAA GAA AAT TAT GGT GTA GTG TCT ACG TAT GAT AGC AGT TTA TCT TCG<br>Glu Glu Asn Tyr Gly Val Val Ser Thr Tyr Asp Ser Ser Leu Ser Ser<br>405 410 415 420 | | 1422 |
| TAT ACA GTG CCC TTA GAA AGA GAT AAC TCA GAA GAA TTT TTA AAA CGG<br>Tyr Thr Val Pro Leu Glu Arg Asp Asn Ser Glu Glu Phe Leu Lys Arg<br>425 430 435 | | 1470 |
| GAA GCA AGG GCA AAC CAG TTA GCA GAA GAA ATT GAG TCA AGT GCC CAG<br>Glu Ala Arg Ala Asn Gln Leu Ala Glu Glu Ile Glu Ser Ser Ala Gln<br>440 445 450 | | 1518 |
| TAC AAA GCT CGA GTG GCC CTG GAA AAT GAT GAT AGG AGT GAG GAA GAA<br>Tyr Lys Ala Arg Val Ala Leu Glu Asn Asp Asp Arg Ser Glu Glu Glu<br>455 460 465 | | 1566 |
| AAA TAC ACA GCA GTT CAG AGA AAT TCC AGT GAA CGT GAG GGG CAC AGC<br>Lys Tyr Thr Ala Val Gln Arg Asn Ser Ser Glu Arg Glu Gly His Ser<br>470 475 480 | | 1614 |
| ATA AAC ACT AGG GAA AAT AAA TAT ATT CCT CCT GGA CAA AGA AAT AGA<br>Ile Asn Thr Arg Glu Asn Lys Tyr Ile Pro Pro Gly Gln Arg Asn Arg<br>485 490 495 500 | | 1662 |
| GAA GTC ATA TCC TGG GGA AGT GGG AGA CAG AAT TCA CCG CGT ATG GGC<br>Glu Val Ile Ser Trp Gly Ser Gly Arg Gln Asn Ser Pro Arg Met Gly<br>505 510 515 | | 1710 |
| CAG CCT GGA TCG GGC TCC ATG CCA TCA AGA TCC ACT TCT CAC ACT TCA<br>Gln Pro Gly Ser Gly Ser Met Pro Ser Arg Ser Thr Ser His Thr Ser<br>520 525 530 | | 1758 |
| GAT TTC AAC CCG AAT TCT GGT TCA GAC CAA AGA GTA GTT AAT GGA GGT<br>Asp Phe Asn Pro Asn Ser Gly Ser Asp Gln Arg Val Val Asn Gly Gly<br>535 540 545 | | 1806 |
| GTT CCC TGG CCA TCG CCT TGC CCA TCT CCT TCC TCT CGC CCA CCT TCT<br>Val Pro Trp Pro Ser Pro Cys Pro Ser Pro Ser Ser Arg Pro Pro Ser<br>550 555 560 | | 1854 |
| CGC TAC CAG TCA GGT CCC AAC TCT CTT CCA CCT CGG GCA GCC ACC CCT<br>Arg Tyr Gln Ser Gly Pro Asn Ser Leu Pro Pro Arg Ala Ala Thr Pro<br>565 570 575 580 | | 1902 |
| ACA CGG CCG CCC TCC AGG CCC CCC TCG CGG CCA TCC AGA CCC CCG TCT<br>Thr Arg Pro Pro Ser Arg Pro Pro Ser Arg Pro Ser Arg Pro Pro Ser<br>585 590 595 | | 1950 |
| CAC CCC TCT GCT CAT GGT TCT CCA GCT CCT GTC TCT ACT ATG CCT AAA<br>His Pro Ser Ala His Gly Ser Pro Ala Pro Val Ser Thr Met Pro Lys<br>600 605 610 | | 1998 |
| CGC ATG TCT TCA GAA GGG CCT CCA AGG ATG TCC CCA AAG GCC CAG CGA<br>Arg Met Ser Ser Glu Gly Pro Pro Arg Met Ser Pro Lys Ala Gln Arg<br>615 620 625 | | 2046 |
| CAT CCT CGA AAT CAC AGA GTT TCT GCT GGG AGG GGT TCC ATA TCC AGT<br>His Pro Arg Asn His Arg Val Ser Ala Gly Arg Gly Ser Ile Ser Ser<br>630 635 640 | | 2094 |
| GGC CTA GAA TTT GTA TCC CAC AAC CCA CCC AGT GAA GCA GCT ACT CCT<br>Gly Leu Glu Phe Val Ser His Asn Pro Pro Ser Glu Ala Ala Thr Pro<br>645 650 655 660 | | 2142 |
| CCA GTA GCA AGG ACC AGT CCC TCG GGG GGA ACG TGG TCA TCA GTG GTC<br>Pro Val Ala Arg Thr Ser Pro Ser Gly Gly Thr Trp Ser Ser Val Val<br>665 670 675 | | 2190 |
| AGT GGG GTT CCA AGA TTA TCC CCT AAA ACT CAT AGA CCC AGG TCT CCC<br>Ser Gly Val Pro Arg Leu Ser Pro Lys Thr His Arg Pro Arg Ser Pro<br>680 685 690 | | 2238 |
| AGA CAG AAC AGT ATT GGA AAT ACC CCC AGT GGG CCA GTT CTT GCT TCT<br>Arg Gln Asn Ser Ile Gly Asn Thr Pro Ser Gly Pro Val Leu Ala Ser | | 2286 |

-continued

|     |     |     | 695 |     |     |     | 700 |     |     |     | 705 |     |     |     |      |
| --- | --- | --- | --- | --- | --- | --- | --- | --- | --- | --- | --- | --- | --- | --- | ---- |
| CCC | CAA | GCT | GGT | ATT | ATT | CCA | ACT | GAA | GCT | GTT | GCC | ATG | CCT | ATT | CCA  | 2334 |
| Pro | Gln | Ala | Gly | Ile | Ile | Pro | Thr | Glu | Ala | Val | Ala | Met | Pro | Ile | Pro  |
|     | 710 |     |     |     | 715 |     |     |     |     | 720 |     |     |     |     |      |
| GCT | GCA | TCT | CCT | ACG | CCT | GCT | AGT | CCT | GCA | TCG | AAC | AGA | GCT | GTT | ACC  | 2382 |
| Ala | Ala | Ser | Pro | Thr | Pro | Ala | Ser | Pro | Ala | Ser | Asn | Arg | Ala | Val | Thr  |
| 725 |     |     |     | 730 |     |     |     | 735 |     |     |     |     | 740 |     |      |
| CCT | TCT | AGT | GAG | GCT | AAA | GAT | TCC | AGG | CTT | CAA | GAT | CAG | AGG | CAG | AAC  | 2430 |
| Pro | Ser | Ser | Glu | Ala | Lys | Asp | Ser | Arg | Leu | Gln | Asp | Gln | Arg | Gln | Asn  |
|     |     |     | 745 |     |     |     | 750 |     |     |     | 755 |     |     |     |      |
| TCT | CCT | GCA | GGG | AAT | AAA | GAA | AAT | ATT | AAA | CCC | AAT | GAA | ACA | TCA | CCT  | 2478 |
| Ser | Pro | Ala | Gly | Asn | Lys | Glu | Asn | Ile | Lys | Pro | Asn | Glu | Thr | Ser | Pro  |
|     |     |     | 760 |     |     |     | 765 |     |     |     | 770 |     |     |     |      |
| AGC | TTC | TCA | AAA | GCT | GAA | AAC | AAA | GGT | ATA | TCA | CCA | GTT | GTT | TCT | GAA  | 2526 |
| Ser | Phe | Ser | Lys | Ala | Glu | Asn | Lys | Gly | Ile | Ser | Pro | Val | Val | Ser | Glu  |
|     |     | 775 |     |     |     | 780 |     |     |     | 785 |     |     |     |     |      |
| CAT | AGA | AAA | CAG | ATT | GAT | GAT | TTA | AAG | AAA | TTT | AAG | AAT | GAT | TTT | AGG  | 2574 |
| His | Arg | Lys | Gln | Ile | Asp | Asp | Leu | Lys | Lys | Phe | Lys | Asn | Asp | Phe | Arg  |
|     | 790 |     |     |     | 795 |     |     |     | 800 |     |     |     |     |     |      |
| TTA | CAG | CCA | AGT | TCT | ACT | TCT | GAA | TCT | ATG | GAT | CAA | CTA | CTA | AAC | AAA  | 2622 |
| Leu | Gln | Pro | Ser | Ser | Thr | Ser | Glu | Ser | Met | Asp | Gln | Leu | Leu | Asn | Lys  |
| 805 |     |     |     | 810 |     |     |     | 815 |     |     |     |     |     |     | 820  |
| AAT | AGA | GAG | GGA | GAA | AAA | TCA | AGA | GAT | TTG | ATC | AAA | GAC | AAA | ATT | GAA  | 2670 |
| Asn | Arg | Glu | Gly | Glu | Lys | Ser | Arg | Asp | Leu | Ile | Lys | Asp | Lys | Ile | Glu  |
|     |     |     | 825 |     |     |     | 830 |     |     |     |     |     | 835 |     |      |
| CCA | AGT | GCT | AAG | GAT | TCT | TTC | ATT | GAA | AAT | AGC | AGC | AGC | AAC | TGT | ACC  | 2718 |
| Pro | Ser | Ala | Lys | Asp | Ser | Phe | Ile | Glu | Asn | Ser | Ser | Ser | Asn | Cys | Thr  |
|     |     | 840 |     |     |     | 845 |     |     |     | 850 |     |     |     |     |      |
| AGT | GGC | AGC | AGC | AAG | CCG | AAT | AGC | CCC | AGC | ATT | TCC | CCT | TCA | ATA | CTT  | 2766 |
| Ser | Gly | Ser | Ser | Lys | Pro | Asn | Ser | Pro | Ser | Ile | Ser | Pro | Ser | Ile | Leu  |
|     | 855 |     |     |     |     | 860 |     |     |     | 865 |     |     |     |     |      |
| AGT | AAC | ACG | GAG | CAC | AAG | AGG | GGA | CCT | GAG | GTC | ACT | TCC | CAA | GGG | GTT  | 2814 |
| Ser | Asn | Thr | Glu | His | Lys | Arg | Gly | Pro | Glu | Val | Thr | Ser | Gln | Gly | Val  |
| 870 |     |     |     |     | 875 |     |     |     | 880 |     |     |     |     |     |      |
| CAG | ACT | TCC | AGC | CCA | GCA | TGT | AAA | CAA | GAG | AAA | GAC | GAT | AAG | GAA | GAG  | 2862 |
| Gln | Thr | Ser | Ser | Pro | Ala | Cys | Lys | Gln | Glu | Lys | Asp | Asp | Lys | Glu | Glu  |
| 885 |     |     |     | 890 |     |     |     | 895 |     |     |     |     |     |     | 900  |
| AAG | AAA | GAC | GCA | GCT | GAG | CAA | GTT | AGG | AAA | TCA | ACA | TTG | AAT | CCC | AAT  | 2910 |
| Lys | Lys | Asp | Ala | Ala | Glu | Gln | Val | Arg | Lys | Ser | Thr | Leu | Asn | Pro | Asn  |
|     |     |     |     | 905 |     |     |     | 910 |     |     |     | 915 |     |     |      |
| GCA | AAG | GAG | TTC | AAC | CCA | CGT | TCC | TTC | TCT | CAG | CCA | AAG | CCT | TCT | ACT  | 2958 |
| Ala | Lys | Glu | Phe | Asn | Pro | Arg | Ser | Phe | Ser | Gln | Pro | Lys | Pro | Ser | Thr  |
|     |     | 920 |     |     |     | 925 |     |     |     | 930 |     |     |     |     |      |
| ACC | CCA | ACT | TCA | CCT | CGG | CCT | CAA | GCA | CAA | CCT | AGC | CCA | TCT | ATG | GTG  | 3006 |
| Thr | Pro | Thr | Ser | Pro | Arg | Pro | Gln | Ala | Gln | Pro | Ser | Pro | Ser | Met | Val  |
|     | 935 |     |     |     | 940 |     |     |     | 945 |     |     |     |     |     |      |
| GGT | CAT | CAA | CAG | CCA | ACT | CCA | GTT | TAT | ACT | CAG | CCT | GTT | TGT | TTT | GCA  | 3054 |
| Gly | His | Gln | Gln | Pro | Thr | Pro | Val | Tyr | Thr | Gln | Pro | Val | Cys | Phe | Ala  |
|     | 950 |     |     |     | 955 |     |     |     | 960 |     |     |     |     |     |      |
| CCA | AAT | ATG | ATG | TAT | CCA | GTC | CCA | GTG | AGC | CCA | GGC | GTG | CAA | CCT | TTA  | 3102 |
| Pro | Asn | Met | Met | Tyr | Pro | Val | Pro | Val | Ser | Pro | Gly | Val | Gln | Pro | Leu  |
| 965 |     |     |     | 970 |     |     |     | 975 |     |     |     | 980 |     |     |      |
| TAC | CCA | ATA | CCT | ATG | ACG | CCC | ATG | CCA | GTG | AAT | CAA | GCC | AAG | ACA | TAT  | 3150 |
| Tyr | Pro | Ile | Pro | Met | Thr | Pro | Met | Pro | Val | Asn | Gln | Ala | Lys | Thr | Tyr  |
|     |     | 985 |     |     |     | 990 |     |     |     | 995 |     |     |     |     |      |
| AGA | GCA | GTA | CCA | AAT | ATG | CCC | CAA | CAG | CGG | CAA | GAC | CAG | CAT | CAT | CAG  | 3198 |
| Arg | Ala | Val | Pro | Asn | Met | Pro | Gln | Gln | Arg | Gln | Asp | Gln | His | His | Gln  |
|     |     | 1000|     |     |     | 1005|     |     |     | 1010|     |     |     |     |      |
| AGT | GCC | ATG | ATG | CAC | CCA | GCG | TCA | GCA | GCG | GGC | CCA | CCG | ATT | GCA | GCC  | 3246 |

```
Ser Ala Met Met His Pro Ala Ser Ala Ala Gly Pro Pro Ile Ala Ala
        1015                1020                1025

ACC CCA CCA GCT TAC TCC ACG CAA TAT GTT GCC TAC AGT CCT CAG CAG         3294
Thr Pro Pro Ala Tyr Ser Thr Gln Tyr Val Ala Tyr Ser Pro Gln Gln
    1030                1035                1040

TTC CCA AAT CAG CCC CTT GTT CAG CAT GTG CCA CAT TAT CAG TCT CAG         3342
Phe Pro Asn Gln Pro Leu Val Gln His Val Pro His Tyr Gln Ser Gln
1045                1050                1055                1060

CAT CCT CAT GTC TAT AGT CCT GTA ATA CAG GGT AAT GCT AGA ATG ATG         3390
His Pro His Val Tyr Ser Pro Val Ile Gln Gly Asn Ala Arg Met Met
            1065                1070                1075

GCA CCA CCA ACA CAC GCC CAG CCT GGT TTA GTA TCT TCT TCA GCA ACT         3438
Ala Pro Pro Thr His Ala Gln Pro Gly Leu Val Ser Ser Ser Ala Thr
        1080                1085                1090

CAG TAC GGG GCT CAT GAG CAG ACG CAT GCG ATG TAT GCA TGT CCC AAA         3486
Gln Tyr Gly Ala His Glu Gln Thr His Ala Met Tyr Ala Cys Pro Lys
    1095                1100                1105

TTA CCA TAC AAC AAG GAG ACA AGC CCT TCT TTC TAC TTT GCC ATT TCC         3534
Leu Pro Tyr Asn Lys Glu Thr Ser Pro Ser Phe Tyr Phe Ala Ile Ser
1110                1115                1120

ACG GGC TCC CTT GCT CAG CAG TAT GCG CAC CCT AAC GCT ACC CTG CAC         3582
Thr Gly Ser Leu Ala Gln Gln Tyr Ala His Pro Asn Ala Thr Leu His
1125                1130                1135                1140

CCA CAT ACT CCA CAC CCT CAG CCT TCA GCT ACC CCC ACT GGA CAG CAG         3630
Pro His Thr Pro His Pro Gln Pro Ser Ala Thr Pro Thr Gly Gln Gln
            1145                1150                1155

CAA AGC CAA CAT GGT GGA AGT CAT CCT GCA CCC AGT CCT GTT CAG CAC         3678
Gln Ser Gln His Gly Gly Ser His Pro Ala Pro Ser Pro Val Gln His
        1160                1165                1170

CAT CAG CAC CAG GCC GCC CAG GCT CTC CAT CTG GCC AGT CCA CAG CAG         3726
His Gln His Gln Ala Ala Gln Ala Leu His Leu Ala Ser Pro Gln Gln
    1175                1180                1185

CAG TCA GCC ATT TAC CAC GCG GGG CTT GCG CCA ACT CCA CCC TCC ATG         3774
Gln Ser Ala Ile Tyr His Ala Gly Leu Ala Pro Thr Pro Pro Ser Met
    1190                1195                1200

ACA CCT GCC TCC AAC ACG CAG TCG CCA CAG AAT AGT TTC CCA GCA GCA         3822
Thr Pro Ala Ser Asn Thr Gln Ser Pro Gln Asn Ser Phe Pro Ala Ala
1205                1210                1215                1220

CAA CAG ACT GTC TTT ACG ATC CAT CCT TCT CAC GTT CAG CCG GCG TAT         3870
Gln Gln Thr Val Phe Thr Ile His Pro Ser His Val Gln Pro Ala Tyr
        1225                1230                1235

ACC AAC CCA CCC CAC ATG GCC CAC GTA CCT CAG GCT CAT GTA CAG TCA         3918
Thr Asn Pro Pro His Met Ala His Val Pro Gln Ala His Val Gln Ser
            1240                1245                1250

GGA ATG GTT CCT TCT CAT CCA ACT GCC CAT GCG CCA ATG ATG CTA ATG         3966
Gly Met Val Pro Ser His Pro Thr Ala His Ala Pro Met Met Leu Met
        1255                1260                1265

ACG ACA CAG CCA CCC GGC GGT CCC CAG GCC GCC CTC GCT CAA AGT GCA         4014
Thr Thr Gln Pro Pro Gly Gly Pro Gln Ala Ala Leu Ala Gln Ser Ala
    1270                1275                1280

CTA CAG CCC ATT CCA GTC TCG ACA ACA GCG CAT TTC CCC TAT ATG ACG         4062
Leu Gln Pro Ile Pro Val Ser Thr Thr Ala His Phe Pro Tyr Met Thr
1285                1290                1295                1300

CAC CCT TCA GTA CAA GCC CAC CAC CAA CAG CAG TTG TAAGGCTGCC              4108
His Pro Ser Val Gln Ala His His Gln Gln Gln Leu
        1305                1310

CTGGAGGAAC CGAAAGGCCA AATTCCCTCC TCCCTTCTAC TGCTTCTACC AACTGGAAGC       4168

ACAGAAAACT AGAATTTCAT TTATTTTGTT TTTAAAATAT ATATGTTGAT TTCTTGTAAC       4228
```

```
ATCCAATAGG AATGCTAACA GTTCACTTGC AGTGGAAGAT ACTTGGACCG AGTAGAGGCA   4288

TTTAGGAACT TGGGGGCTAT TCCATAATTC CATATGCTGT TTCAGAGTCC CGCAGGTACC   4348

CCAGCTCTGC TTGCCGAAAC TGGAAGTTAT TTATTTTTTA ATAACCCTTG AAAGTCATGA   4408

ACACATCAGC TAGCAAAAGA AGTAACAAGA GTGATTCTTG CTGCTATTAC TGCTAAAAAA   4468

AAAAAAAAAA AAA                                                     4481
```

(2) INFORMATION FOR SEQ ID NO:3:

(i) SEQUENCE CHARACTERISTICS:
        (A) LENGTH: 1312 amino acids
        (B) TYPE: amino acid
        (D) TOPOLOGY: linear (ii) MOLECULE TYPE: protein (xi) SEQUENCE DESCRIPTION: SEQ ID NO:3:

```
Met Arg Ser Ala Ala Ala Ala Pro Arg Ser Pro Ala Val Ala Thr Glu
  1               5                  10                  15

Ser Arg Arg Phe Ala Ala Ala Arg Trp Pro Gly Trp Arg Ser Leu Gln
                 20                  25                  30

Arg Pro Ala Arg Arg Ser Gly Arg Gly Gly Gly Ala Ala Pro Gly
             35                  40                  45

Pro Tyr Pro Ser Ala Ala Pro Pro Pro Gly Pro Gly Pro Pro Pro
 50                  55                  60

Ser Arg Gln Ser Ser Pro Pro Ser Ala Ser Asp Cys Phe Gly Ser Asn
 65                  70                  75                  80

Gly Asn Gly Gly Gly Ala Phe Arg Pro Gly Ser Arg Arg Leu Leu Gly
                 85                  90                  95

Leu Gly Gly Pro Pro Arg Pro Phe Val Val Leu Leu Pro Leu Ala
                100                 105                 110

Ser Pro Gly Ala Pro Pro Ala Ala Pro Thr Arg Ala Ser Pro Leu Gly
                115                 120                 125

Ala Arg Ala Ser Pro Pro Arg Ser Gly Val Ser Leu Ala Arg Pro Ala
            130                 135                 140

Pro Gly Cys Pro Arg Pro Ala Cys Glu Pro Val Tyr Gly Pro Leu Thr
145                 150                 155                 160

Met Ser Leu Lys Pro Gln Gln Gln Gln Gln Gln Gln Gln Gln Gln
                165                 170                 175

Gln Gln Gln Gln Gln Gln Gln Gln Gln Gln Pro Pro Ala Ala
            180                 185                 190

Ala Asn Val Arg Lys Pro Gly Gly Ser Gly Leu Leu Ala Ser Pro Ala
            195                 200                 205

Ala Ala Pro Ser Pro Ser Ser Ser Val Ser Ser Ser Ala Thr
            210                 215                 220

Ala Pro Ser Ser Val Val Ala Ala Thr Ser Gly Gly Arg Pro Gly
225                 230                 235                 240

Leu Gly Arg Gly Arg Asn Ser Asn Lys Gly Leu Pro Gln Ser Thr Ile
                245                 250                 255

Ser Phe Asp Gly Ile Tyr Ala Asn Met Arg Met Val His Ile Leu Thr
                260                 265                 270

Ser Val Val Gly Ser Lys Cys Glu Val Gln Val Lys Asn Gly Gly Ile
            275                 280                 285

Tyr Glu Gly Val Phe Lys Thr Tyr Ser Pro Lys Cys Asp Leu Val Leu
290                 295                 300
```

-continued

```
Asp Ala Ala His Glu Lys Ser Thr Glu Ser Ser Ser Gly Pro Lys Arg
305                 310                 315                 320

Glu Glu Ile Met Glu Ser Ile Leu Phe Lys Cys Ser Asp Phe Val Val
                325                 330                 335

Val Gln Phe Lys Asp Met Asp Ser Ser Tyr Ala Lys Arg Asp Ala Phe
                340                 345                 350

Thr Asp Ser Ala Ile Ser Ala Lys Val Asn Gly Glu His Lys Glu Lys
                355                 360                 365

Asp Leu Glu Pro Trp Asp Ala Gly Glu Leu Thr Ala Asn Glu Glu Leu
370                 375                 380

Glu Ala Leu Glu Asn Asp Val Ser Asn Gly Trp Asp Pro Asn Asp Met
385                 390                 395                 400

Phe Arg Tyr Asn Glu Asn Tyr Gly Val Val Ser Thr Tyr Asp Ser
                405                 410                 415

Ser Leu Ser Ser Tyr Thr Val Pro Leu Glu Arg Asp Asn Ser Glu Glu
                420                 425                 430

Phe Leu Lys Arg Glu Ala Arg Ala Asn Gln Leu Ala Glu Glu Ile Glu
                435                 440                 445

Ser Ser Ala Gln Tyr Lys Ala Arg Val Ala Leu Glu Asn Asp Asp Arg
450                 455                 460

Ser Glu Glu Lys Tyr Thr Ala Val Gln Arg Asn Ser Ser Glu Arg
465                 470                 475                 480

Glu Gly His Ser Ile Asn Thr Arg Glu Asn Lys Tyr Ile Pro Pro Gly
                485                 490                 495

Gln Arg Asn Arg Glu Val Ile Ser Trp Gly Ser Gly Arg Gln Asn Ser
                500                 505                 510

Pro Arg Met Gly Gln Pro Gly Ser Gly Ser Met Pro Ser Arg Ser Thr
                515                 520                 525

Ser His Thr Ser Asp Phe Asn Pro Asn Ser Gly Ser Asp Gln Arg Val
530                 535                 540

Val Asn Gly Gly Val Pro Trp Pro Ser Pro Cys Pro Ser Pro Ser Ser
545                 550                 555                 560

Arg Pro Pro Ser Arg Tyr Gln Ser Gly Pro Asn Ser Leu Pro Pro Arg
                565                 570                 575

Ala Ala Thr Pro Thr Arg Pro Pro Ser Arg Pro Pro Ser Arg Pro Ser
                580                 585                 590

Arg Pro Pro Ser His Pro Ser Ala His Gly Ser Pro Ala Pro Val Ser
                595                 600                 605

Thr Met Pro Lys Arg Met Ser Ser Glu Gly Pro Pro Arg Met Ser Pro
610                 615                 620

Lys Ala Gln Arg His Pro Arg Asn His Arg Val Ser Ala Gly Arg Gly
625                 630                 635                 640

Ser Ile Ser Ser Gly Leu Glu Phe Val Ser His Asn Pro Pro Ser Glu
                645                 650                 655

Ala Ala Thr Pro Pro Val Ala Arg Thr Ser Pro Ser Gly Gly Thr Trp
                660                 665                 670

Ser Ser Val Val Ser Gly Val Pro Arg Leu Ser Pro Lys Thr His Arg
                675                 680                 685

Pro Arg Ser Pro Arg Gln Asn Ser Ile Gly Asn Thr Pro Ser Gly Pro
                690                 695                 700

Val Leu Ala Ser Pro Gln Ala Gly Ile Ile Pro Thr Glu Ala Val Ala
705                 710                 715                 720

Met Pro Ile Pro Ala Ala Ser Pro Thr Pro Ala Ser Pro Ala Ser Asn
```

-continued

```
                725                 730                 735
Arg Ala Val Thr Pro Ser Ser Glu Ala Lys Asp Ser Arg Leu Gln Asp
                740                 745                 750
Gln Arg Gln Asn Ser Pro Ala Gly Asn Lys Glu Asn Ile Lys Pro Asn
                755                 760                 765
Glu Thr Ser Pro Ser Phe Ser Lys Ala Glu Asn Lys Gly Ile Ser Pro
            770                 775                 780
Val Val Ser Glu His Arg Lys Gln Ile Asp Asp Leu Lys Lys Phe Lys
785                 790                 795                 800
Asn Asp Phe Arg Leu Gln Pro Ser Ser Thr Ser Glu Ser Met Asp Gln
                    805                 810                 815
Leu Leu Asn Lys Asn Arg Glu Gly Glu Lys Ser Arg Asp Leu Ile Lys
                820                 825                 830
Asp Lys Ile Glu Pro Ser Ala Lys Asp Ser Phe Ile Glu Asn Ser Ser
            835                 840                 845
Ser Asn Cys Thr Ser Gly Ser Ser Lys Pro Asn Ser Pro Ser Ile Ser
850                 855                 860
Pro Ser Ile Leu Ser Asn Thr Glu His Lys Arg Gly Pro Glu Val Thr
865                 870                 875                 880
Ser Gln Gly Val Gln Thr Ser Ser Pro Ala Cys Lys Gln Glu Lys Asp
                    885                 890                 895
Asp Lys Glu Glu Lys Lys Asp Ala Ala Glu Gln Val Arg Lys Ser Thr
                900                 905                 910
Leu Asn Pro Asn Ala Lys Glu Phe Asn Pro Arg Ser Phe Ser Gln Pro
                915                 920                 925
Lys Pro Ser Thr Thr Pro Thr Ser Pro Arg Pro Gln Ala Gln Pro Ser
            930                 935                 940
Pro Ser Met Val Gly His Gln Gln Pro Thr Pro Val Tyr Thr Gln Pro
945                 950                 955                 960
Val Cys Phe Ala Pro Asn Met Met Tyr Pro Val Pro Val Ser Pro Gly
                    965                 970                 975
Val Gln Pro Leu Tyr Pro Ile Pro Met Thr Pro Met Pro Val Asn Gln
                980                 985                 990
Ala Lys Thr Tyr Arg Ala Val Pro Asn Met Pro Gln Gln Arg Gln Asp
            995                 1000                1005
Gln His His Gln Ser Ala Met Met His Pro Ala Ser Ala Ala Gly Pro
        1010                1015                1020
Pro Ile Ala Ala Thr Pro Pro Ala Tyr Ser Thr Gln Tyr Val Ala Tyr
1025                1030                1035                1040
Ser Pro Gln Gln Phe Pro Asn Gln Pro Leu Val Gln His Val Pro His
                    1045                1050                1055
Tyr Gln Ser Gln His Pro His Val Tyr Ser Pro Val Ile Gln Gly Asn
                1060                1065                1070
Ala Arg Met Met Ala Pro Pro Thr His Ala Gln Pro Gly Leu Val Ser
            1075                1080                1085
Ser Ser Ala Thr Gln Tyr Gly Ala His Glu Gln Thr His Ala Met Tyr
        1090                1095                1100
Ala Cys Pro Lys Leu Pro Tyr Asn Lys Glu Thr Ser Pro Ser Phe Tyr
1105                1110                1115                1120
Phe Ala Ile Ser Thr Gly Ser Leu Ala Gln Gln Tyr Ala His Pro Asn
                    1125                1130                1135
Ala Thr Leu His Pro His Thr Pro His Pro Gln Pro Ser Ala Thr Pro
                1140                1145                1150
```

```
Thr Gly Gln Gln Gln Ser Gln His Gly Gly Ser His Pro Ala Pro Ser
        1155                1160                1165

Pro Val Gln His His Gln His Gln Ala Ala Gln Ala Leu His Leu Ala
    1170                1175                1180

Ser Pro Gln Gln Gln Ser Ala Ile Tyr His Ala Gly Leu Ala Pro Thr
1185                1190                1195                1200

Pro Pro Ser Met Thr Pro Ala Ser Asn Thr Gln Ser Pro Gln Asn Ser
                1205                1210                1215

Phe Pro Ala Ala Gln Gln Thr Val Phe Thr Ile His Pro Ser His Val
            1220                1225                1230

Gln Pro Ala Tyr Thr Asn Pro Pro His Met Ala His Val Pro Gln Ala
        1235                1240                1245

His Val Gln Ser Gly Met Val Pro Ser His Pro Thr Ala His Ala Pro
    1250                1255                1260

Met Met Leu Met Thr Thr Gln Pro Pro Gly Gly Pro Gln Ala Ala Leu
1265                1270                1275                1280

Ala Gln Ser Ala Leu Gln Pro Ile Pro Val Ser Thr Thr Ala His Phe
                1285                1290                1295

Pro Tyr Met Thr His Pro Ser Val Gln Ala His His Gln Gln Gln Leu
            1300                1305                1310

(2) INFORMATION FOR SEQ ID NO:4:

(i) SEQUENCE CHARACTERISTICS:
        (A) LENGTH: 1257 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 2..1255

(xi) SEQUENCE DESCRIPTION: SEQ ID NO:4:

G CAC GAG GGG CCG CTC ACC ATG TCG CTG AAG CCG CAG CCG CAG CCG         46
  His Glu Gly Pro Leu Thr Met Ser Leu Lys Pro Gln Pro Gln Pro
  1               5                   10                  15

CCC GCG CCC GCC ACT GGC CGC AAG CCC GGC GGC GGC CTG CTC TCG TCG       94
Pro Ala Pro Ala Thr Gly Arg Lys Pro Gly Gly Gly Leu Leu Ser Ser
            20                  25                  30

CCC GGC GCC GCG CCG GCC TCG GCC GCG GTG ACC TCG GCT TCC GTG GTG      142
Pro Gly Ala Ala Pro Ala Ser Ala Ala Val Thr Ser Ala Ser Val Val
        35                  40                  45

CCG GCC CCG GCC GCG CCG GTG GCG TCT TCC TCG GCG GCC GCG GGC GGC      190
Pro Ala Pro Ala Ala Pro Val Ala Ser Ser Ser Ala Ala Ala Gly Gly
    50                  55                  60

GGG CGT CCC GGC CTG GGC AGA GGT CGG AAC AGT AGC AAA GGA CTG CCT      238
Gly Arg Pro Gly Leu Gly Arg Gly Arg Asn Ser Ser Lys Gly Leu Pro
65                  70                  75

CAG CCT ACG ATT TCT TTT GAT GGA ATC TAT GCA AAC GTG AGG ATG GTT      286
Gln Pro Thr Ile Ser Phe Asp Gly Ile Tyr Ala Asn Val Arg Met Val
            80                  85                  90                  95

CAT ATA CTT ACG TCA GTT GTT GGA TCG AAA TGT GAA GTA CAA GTG AAA      334
His Ile Leu Thr Ser Val Val Gly Ser Lys Cys Glu Val Gln Val Lys
                100                 105                 110

AAC GGA GGC ATA TAT GAA GGA GTT TTT AAA ACA TAC AGT CCT AAG TGT      382
Asn Gly Gly Ile Tyr Glu Gly Val Phe Lys Thr Tyr Ser Pro Lys Cys
            115                 120                 125
```

```
GAC TTG GTA CTT GAT GCT GCA CAT GAG AAA AGT ACA GAA TCC AGT TCG         430
Asp Leu Val Leu Asp Ala Ala His Glu Lys Ser Thr Glu Ser Ser Ser
        130                 135                 140

GGG CCA AAA CGT GAA GAA ATA ATG GAG AGT GTT TTG TTC AAA TGC TCA         478
Gly Pro Lys Arg Glu Glu Ile Met Glu Ser Val Leu Phe Lys Cys Ser
        145                 150                 155

GAC TTC GTT GTG GTA CAG TTT AAA GAT ACA GAC TCC AGT TAT GCA CGG         526
Asp Phe Val Val Val Gln Phe Lys Asp Thr Asp Ser Ser Tyr Ala Arg
160                 165                 170                 175

AGA GAT GCT TTT ACT GAC TCT GCT CTC AGC GCA AAG GTG AAT GGT GAG         574
Arg Asp Ala Phe Thr Asp Ser Ala Leu Ser Ala Lys Val Asn Gly Glu
                180                 185                 190

CAC AAG GAG AAG GAC CTG GAG CCC TGG GAT GCA GGG GAG CTC ACG GCC         622
His Lys Glu Lys Asp Leu Glu Pro Trp Asp Ala Gly Glu Leu Thr Ala
            195                 200                 205

AGC GAG GAG CTG GAG CTG GAG AAT GAT GTG TCT AAT GGA TGG GAC CCC         670
Ser Glu Glu Leu Glu Leu Glu Asn Asp Val Ser Asn Gly Trp Asp Pro
        210                 215                 220

AAT GAC ATG TTT CGA TAT AAT GAA GAG AAT TAT GGT GTG GTG TCC ACA         718
Asn Asp Met Phe Arg Tyr Asn Glu Glu Asn Tyr Gly Val Val Ser Thr
    225                 230                 235

TAT GAT AGC AGT TTA TCT TCA TAT ACG GTT CCT TTA GAA AGG GAC AAC         766
Tyr Asp Ser Ser Leu Ser Ser Tyr Thr Val Pro Leu Glu Arg Asp Asn
240                 245                 250                 255

TCA GAA GAA TTT CTT AAA CGG GAG GCA AGG GCA AAC CAG TTA GCA GAA         814
Ser Glu Glu Phe Leu Lys Arg Glu Ala Arg Ala Asn Gln Leu Ala Glu
                260                 265                 270

GAA ATT GAA TCC AGT GCT CAG TAC AAA GCT CGT GTC GCC CTT GAG AAT         862
Glu Ile Glu Ser Ser Ala Gln Tyr Lys Ala Arg Val Ala Leu Glu Asn
            275                 280                 285

GAT GAC CGG AGT GAG GAA GAA AAA TAC ACA GCA GTC CAG AGA AAC TGC         910
Asp Asp Arg Ser Glu Glu Glu Lys Tyr Thr Ala Val Gln Arg Asn Cys
        290                 295                 300

AGT GAC CGG GAG GGG CAT GGC CCC AAC ACT AGG GAC AAT AAA TAT ATT         958
Ser Asp Arg Glu Gly His Gly Pro Asn Thr Arg Asp Asn Lys Tyr Ile
    305                 310                 315

CCT CCT GGA CAA AGA AAC AGA GAA GTC CTA TCC TGG GGA AGT GGG AGA        1006
Pro Pro Gly Gln Arg Asn Arg Glu Val Leu Ser Trp Gly Ser Gly Arg
320                 325                 330                 335

CAG AGC TCA CCA CGG ATG GGC CAG CCT GGG CCA GGC TCC ATG CCG TCA        1054
Gln Ser Ser Pro Arg Met Gly Gln Pro Gly Pro Gly Ser Met Pro Ser
                340                 345                 350

AGA GCT GCT TCT CAC ACT TCA GAT TTC AAC CCG AAC GCT GGC TCA GAC        1102
Arg Ala Ala Ser His Thr Ser Asp Phe Asn Pro Asn Ala Gly Ser Asp
            355                 360                 365

CAA AGA GTA GTT AAT GGA GGT GTT CCC TGG CCA TCG CCT TGC CCA TCT        1150
Gln Arg Val Val Asn Gly Gly Val Pro Trp Pro Ser Pro Cys Pro Ser
        370                 375                 380

CCT TCC TCT CGC CCA CCT TCT CGC TAC CAG TCA GGT CCC AAC TCT CTT        1198
Pro Ser Ser Arg Pro Pro Ser Arg Tyr Gln Ser Gly Pro Asn Ser Leu
    385                 390                 395

CCA CCT CGG GCA GCC ACC CCT ACA CGG CCT CGT GCC GAA TTC CTG CAG        1246
Pro Pro Arg Ala Ala Thr Pro Thr Arg Pro Arg Ala Glu Phe Leu Gln
400                 405                 410                 415

CCC GGG GAT CC                                                         1257
Pro Gly Asp (2) INFORMATION FOR SEQ ID NO:5:
```

```
     (i) SEQUENCE CHARACTERISTICS:
          (A) LENGTH: 418 amino acids
          (B) TYPE: amino acid
          (D) TOPOLOGY: linear (ii) MOLECULE TYPE: protein (xi) SEQUENCE DESCRIPTION: SEQ ID NO:5:

His Glu Gly Pro Leu Thr Met Ser Leu Lys Pro Gln Pro Gln Pro Pro
 1               5                  10                  15

Ala Pro Ala Thr Gly Arg Lys Pro Gly Gly Gly Leu Leu Ser Ser Pro
            20                  25                  30

Gly Ala Ala Pro Ala Ser Ala Ala Val Thr Ser Ala Ser Val Val Pro
        35                  40                  45

Ala Pro Ala Ala Pro Val Ala Ser Ser Ala Ala Ala Gly Gly Gly
    50                  55                  60

Arg Pro Gly Leu Gly Arg Gly Arg Asn Ser Ser Lys Gly Leu Pro Gln
65                  70                  75                  80

Pro Thr Ile Ser Phe Asp Gly Ile Tyr Ala Asn Val Arg Met Val His
                85                  90                  95

Ile Leu Thr Ser Val Val Gly Ser Lys Cys Glu Val Gln Val Lys Asn
            100                 105                 110

Gly Gly Ile Tyr Glu Gly Val Phe Lys Thr Tyr Ser Pro Lys Cys Asp
        115                 120                 125

Leu Val Leu Asp Ala Ala His Glu Lys Ser Thr Glu Ser Ser Ser Gly
    130                 135                 140

Pro Lys Arg Glu Glu Ile Met Glu Ser Val Leu Phe Lys Cys Ser Asp
145                 150                 155                 160

Phe Val Val Val Gln Phe Lys Asp Thr Asp Ser Ser Tyr Ala Arg Arg
                165                 170                 175

Asp Ala Phe Thr Asp Ser Ala Leu Ser Ala Lys Val Asn Gly Glu His
            180                 185                 190

Lys Glu Lys Asp Leu Glu Pro Trp Asp Ala Gly Glu Leu Thr Ala Ser
        195                 200                 205

Glu Glu Leu Glu Leu Glu Asn Asp Val Ser Asn Gly Trp Asp Pro Asn
    210                 215                 220

Asp Met Phe Arg Tyr Asn Glu Glu Asn Tyr Gly Val Val Ser Thr Tyr
225                 230                 235                 240

Asp Ser Ser Leu Ser Ser Tyr Thr Val Pro Leu Glu Arg Asp Asn Ser
                245                 250                 255

Glu Glu Phe Leu Lys Arg Glu Ala Arg Ala Asn Gln Leu Ala Glu Glu
            260                 265                 270

Ile Glu Ser Ser Ala Gln Tyr Lys Ala Arg Val Ala Leu Glu Asn Asp
        275                 280                 285

Asp Arg Ser Glu Glu Lys Tyr Thr Ala Val Gln Arg Asn Cys Ser
    290                 295                 300

Asp Arg Glu Gly His Gly Pro Asn Thr Arg Asp Asn Lys Tyr Ile Pro
305                 310                 315                 320

Pro Gly Gln Arg Asn Arg Glu Val Leu Ser Trp Gly Ser Gly Arg Gln
                325                 330                 335

Ser Ser Pro Arg Met Gly Gln Pro Gly Pro Gly Ser Met Pro Ser Arg
            340                 345                 350

Ala Ala Ser His Thr Ser Asp Phe Asn Pro Asn Ala Gly Ser Asp Gln
        355                 360                 365

Arg Val Val Asn Gly Gly Val Pro Trp Pro Ser Pro Cys Pro Ser Pro
```

```
                370               375               380
Ser Ser Arg Pro Pro Ser Arg Tyr Gln Ser Gly Pro Asn Ser Leu Pro
385               390               395               400

Pro Arg Ala Ala Thr Pro Thr Arg Pro Arg Ala Glu Phe Leu Gln Pro
              405               410               415

Gly Asp
```

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
GGGCCCCTCA CCATGTCG                                              18
```

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CGGGCTTGCG GACATTGG                                              18
```

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
CCGCGGCTGC CAATGTCC                                              18
```

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
GTAACCGTTC GGCGCCCG                                              18
```

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GGCTCCCGGC GGCTCCTT                                                   18

(2) INFORMATION FOR SEQ ID NO:11:

(i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:11:

TGCTGCTGCT GCTGGGGCTT CAG                                             23

(2) INFORMATION FOR SEQ ID NO:12:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:12:

CCGCCCGCTC CTCACGTGT                                                  19

(2) INFORMATION FOR SEQ ID NO:13:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:13:

ACCCCCGAGA AAGCAACC                                                   18

(2) INFORMATION FOR SEQ ID NO:14:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:14:

CCGTTGCCGT TGCTACCA                                                   18

(2) INFORMATION FOR SEQ ID NO:15:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:15:

```
TTCTCATGTG CGGCATCAAG                                                   20
```

(2) INFORMATION FOR SEQ ID NO:16:

(i) SEQUENCE CHARACTERISTICS:
        (A) LENGTH: 346 amino acids
        (B) TYPE: amino acid
        (C) STRANDEDNESS: single
        (D) TOPOLOGY: linear (ii) MOLECULE TYPE: RNA (genomic)

(xi) SEQUENCE DESCRIPTION: SEQ ID NO:16:

```
Val Tyr Gly Pro Leu Thr Met Ser Leu Lys Pro Gln Gln Gln Gln
1               5                   10                  15

Gln Gln Gln Gln Gln Gln Gln Gln Gln Gln Gln Gln Gln Gln Gln
            20                  25                  30

Gln Pro Pro Ala Ala Ala Asn Val Arg Lys Pro Gly Gly Ser Gly
            35                  40                  45

Leu Leu Ala Ser Pro Ala Ala Ala Pro Ser Pro Ser Ser Ser Val
            50                  55                  60

Ser Ser Ser Ser Ala Thr Ala Pro Ser Ser Val Val Ala Ala Thr Ser
65                  70                  75                  80

Gly Gly Gly Arg Pro Gly Leu Gly Arg Gly Arg Asn Ser Asn Lys Gly
                85                  90                  95

Leu Pro Gln Ser Thr Ile Ser Phe Asp Gly Ile Tyr Ala Asn Met Arg
            100                 105                 110

Met Val His Ile Leu Thr Ser Val Val Gly Ser Lys Cys Glu Val Gln
            115                 120                 125

Val Lys Asn Gly Gly Ile Tyr Glu Gly Val Phe Lys Thr Tyr Ser Pro
            130                 135                 140

Lys Cys Asp Leu Val Leu Asp Ala Ala His Glu Lys Ser Thr Glu Ser
145                 150                 155                 160

Ser Ser Gly Pro Lys Arg Glu Glu Ile Met Glu Ser Ile Leu Phe Lys
                165                 170                 175

Cys Ser Asp Phe Val Val Val Gln Phe Lys Asp Met Asp Ser Ser Tyr
            180                 185                 190

Ala Lys Arg Asp Ala Phe Thr Asp Ser Ala Ile Ser Ala Lys Val Asn
            195                 200                 205

Gly Glu His Lys Glu Lys Asp Leu Glu Pro Trp Asp Ala Gly Glu Leu
            210                 215                 220

Thr Ala Asn Glu Glu Leu Glu Ala Leu Glu Asn Asp Val Ser Asn Gly
225                 230                 235                 240

Trp Asp Pro Asn Asp Met Phe Arg Tyr Asn Glu Glu Asn Tyr Gly Val
                245                 250                 255

Val Ser Thr Tyr Asp Ser Ser Leu Ser Ser Tyr Thr Val Pro Leu Glu
            260                 265                 270

Arg Asp Asn Ser Glu Glu Phe Leu Lys Arg Glu Ala Arg Ala Asn Gln
            275                 280                 285

Leu Ala Glu Glu Ile Glu Ser Ser Ala Gln Tyr Lys Ala Arg Val Ala
            290                 295                 300

Leu Glu Asn Asp Asp Arg Ser Glu Glu Lys Tyr Thr Ala Val Gln
305                 310                 315                 320

Arg Asn Ser Ser Glu Arg Glu Gly His Ser Ile Asn Thr Arg Glu Asn
                325                 330                 335

Lys Tyr Ile Pro Pro Gly Gln Arg Asn Arg
```

340                    345

(2) INFORMATION FOR SEQ ID NO:17:

(i) SEQUENCE CHARACTERISTICS:
        (A) LENGTH: 326 amino acids
        (B) TYPE: amino acid
        (C) STRANDEDNESS: single
        (D) TOPOLOGY: linear (ii) MOLECULE TYPE: RNA (genomic)

(xi) SEQUENCE DESCRIPTION: SEQ ID NO:17:

```
His Glu Gly Pro Leu Thr Met Ser Leu Lys Pro Gln Pro Gln Pro Pro
1               5                   10                  15

Ala Pro Ala Thr Gly Arg Lys Pro Gly Gly Leu Leu Ser Ser Pro
            20                  25                  30

Gly Ala Ala Pro Ala Ser Ala Ala Val Thr Ser Ala Ser Val Val Pro
        35                  40                  45

Ala Pro Ala Ala Pro Val Ala Ser Ser Ala Ala Gly Gly Gly
50                  55                  60

Arg Pro Gly Leu Gly Arg Gly Arg Asn Ser Ser Lys Gly Leu Pro Gln
65                  70                  75                  80

Pro Thr Ile Ser Phe Asp Gly Ile Tyr Ala Asn Val Arg Met Val His
                85                  90                  95

Ile Leu Thr Ser Val Val Gly Ser Lys Cys Glu Val Gln Val Lys Asn
            100                 105                 110

Gly Gly Ile Tyr Glu Gly Val Phe Lys Thr Tyr Ser Pro Lys Cys Asp
        115                 120                 125

Leu Val Leu Asp Ala Ala His Glu Lys Ser Thr Glu Ser Ser Ser Gly
130                 135                 140

Pro Lys Arg Glu Glu Ile Met Glu Ser Val Leu Phe Lys Cys Ser Asp
145                 150                 155                 160

Phe Val Val Val Gln Phe Lys Asp Thr Asp Ser Ser Tyr Ala Arg Arg
                165                 170                 175

Asp Ala Phe Thr Asp Ser Ala Leu Ser Ala Lys Val Asn Gly Glu His
            180                 185                 190

Lys Glu Lys Asp Leu Glu Pro Trp Asp Ala Gly Glu Leu Thr Ala Ser
        195                 200                 205

Glu Glu Leu Glu Leu Glu Asn Asp Val Ser Asn Gly Trp Asp Pro Asn
210                 215                 220

Asp Met Phe Arg Tyr Asn Glu Glu Asn Tyr Gly Val Val Ser Thr Tyr
225                 230                 235                 240

Asp Ser Ser Leu Ser Ser Tyr Thr Val Pro Leu Glu Arg Asp Asn Ser
                245                 250                 255

Glu Glu Phe Leu Lys Arg Glu Ala Arg Ala Asn Gln Leu Ala Glu Glu
            260                 265                 270

Ile Glu Ser Ser Ala Gln Tyr Lys Ala Arg Val Ala Leu Glu Asn Asp
        275                 280                 285

Asp Arg Ser Glu Glu Lys Tyr Thr Ala Val Gln Arg Asn Cys Ser
290                 295                 300

Asp Arg Glu Gly His Gly Pro Asn Thr Arg Asp Asn Lys Tyr Ile Pro
305                 310                 315                 320

Pro Gly Gln Arg Asn Arg
            325
```

-continued (2) INFORMATION FOR SEQ ID NO:18:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: RNA (genomic)

(xi) SEQUENCE DESCRIPTION: SEQ ID NO:18:

```
Leu Ala Pro Gln Pro Pro Pro Gln Gln His Gln Glu Arg Pro Gly
1               5                  10                 15

Ala Ala Ala Ile Gly Ser Ala Arg Gly Gln Ser Thr Gly Lys Gly Pro
            20                  25                  30

Pro Gln Ser Pro Val Phe Glu Gly Val Tyr Asn Asn Ser Arg Met Leu
        35                  40                  45

His Phe Leu Thr Ala Val Val Gly Ser Thr Cys Asp Val Lys Val Lys
    50                  55                  60

Asn Gly Thr Thr Tyr Glu Gly Ile Phe Lys Thr Leu Ser Ser Lys Phe
65                  70                  75                  80

Glu Leu Ala Val Asp Ala Val His Arg Lys Ala Ser Glu Pro Ala Gly
                85                  90                  95

Gly Pro Arg Arg Glu Asp Ile Val Asp Thr Met Val Phe Lys Pro Ser
            100                 105                 110

Asp Val Met Leu Val His Phe Arg Asn Val Asp Phe Asn Tyr Ala Thr
            115                 120                 125

Lys Asp Lys Phe Thr Asp Ser Ala Ile Ala Met Asn Ser Lys Val Asn
130                 135                 140

Gly Glu His Lys Glu Lys Val Leu Gln Arg Trp Glu Gly Gly Asp Ser
145                 150                 155                 160

Asn Ser Asp Asp Tyr Asp Leu Glu Ser Asp Met Ser Asn Gly Trp Asp
                165                 170                 175

Pro Asn Glu Met Phe Lys Phe Asn Glu Glu Asn Tyr Gly Val Lys Thr
            180                 185                 190

Thr Tyr Asp Ser Ser Leu Ser Ser Tyr Thr Val Pro Leu Glu Lys Asp
        195                 200                 205

Asn Ser Glu Glu Phe Arg Gln Arg Glu Leu Arg Ala Ala Gln Leu Ala
210                 215                 220

Arg Glu Ile Glu Ser Ser Pro Gln Tyr Arg Leu Arg Ile Ala Met Glu
225                 230                 235                 240

Asn Asp Asp Gly Arg Thr Glu Glu Glu Lys His Ser Ala Val Gln Arg
                245                 250                 255

Gln Gly Ser Gly Arg Glu Ser Pro Ser Leu Ala Ser Arg Glu Gly Lys
            260                 265                 270

Tyr Ile Pro
        275
```